US005580925A

United States Patent [19]

Iwahara et al.

[11] Patent Number: 5,580,925
[45] Date of Patent: Dec. 3, 1996

[54] CURABLE ORGANIC POLYMERS CONTAINING HYDROSILYL GROUPS

[75] Inventors: Takahisa Iwahara; Makato Chiba; Tomoko Takahara; Kazuya Yonezawa, all of Kobe, Japan

[73] Assignee: Kanegafuchi Chemical Industry, Co., Ltd., Osaka, Japan

[21] Appl. No.: 601,712

[22] PCT Filed: Feb. 28, 1990

[86] PCT No.: PCT/JP90/00251

§ 371 Date: Oct. 29, 1990

§ 102(e) Date: Oct. 29, 1990

[87] PCT Pub. No.: WO90/10037

PCT Pub. Date: Sep. 7, 1990

[30] Foreign Application Priority Data

| Feb. 28, 1989 | [JP] | Japan | 49545 |
| Mar. 27, 1989 | [JP] | Japan | 74419 |
| Apr. 12, 1989 | [JP] | Japan | 93801 |
| Apr. 24, 1989 | [JP] | Japan | 103646 |
| Apr. 28, 1989 | [JP] | Japan | 109587 |
| Apr. 28, 1989 | [JP] | Japan | 109588 |
| May 12, 1989 | [JP] | Japan | 119483 |
| May 23, 1989 | [JP] | Japan | 130695 |
| Jun. 7, 1989 | [JP] | Japan | 145674 |
| Jun. 15, 1989 | [JP] | Japan | 153143 |

[51] Int. Cl.$^6$ ............................. C08F 299/08
[52] U.S. Cl. .................. 525/100; 525/102; 525/106; 525/326.5; 525/329.7; 525/330.3; 525/331.9; 525/333.1; 525/333.7; 525/342; 525/474; 525/479; 528/10; 528/12; 528/31; 528/33; 528/35

[58] Field of Search ................... 525/100, 106, 525/474, 479, 342

[56] References Cited

U.S. PATENT DOCUMENTS

| 4,334,036 | 6/1982 | Yonezawa | 525/102 |
| 4,520,160 | 5/1985 | Brown | 524/765 |

FOREIGN PATENT DOCUMENTS

| 0183533 | 6/1986 | European Pat. Off. . |
| 54-36395 | 3/1979 | Japan . |
| 55-135136 | 10/1980 | Japan . |
| 55-137129 | 10/1980 | Japan . |

OTHER PUBLICATIONS

Patent Abstracts of Japan, vol. 8, No. 62, Mar. 23, 1984, JPA 58-217505.
Patent Abstracts of Japan, vol. 12, No. 202, Jun. 10, 1988, JPA 63-6041.
Chemicals Patents Index, Basic Abstracts Jnl., SectionA, week 8619, Jul. 2, 19876, JPA 86-121878.

*Primary Examiner*—Fred Zitomer
*Attorney, Agent, or Firm*—Foley & Lardner

[57] ABSTRACT

An organic polymer having at least two hydrosilyl groups in a molecule is mixed with an organic polymer having at least one alkenyl group in a molecule and a hydrosilylation catalyst to give a composition. Such composition is rapidly curable, has good depth curability and gives a cured material having good mechanical properties.

26 Claims, 7 Drawing Sheets

CURABLE ORGANIC POLYMERS CONTAINING HYDROSILYL GROUPS

FIELD OF THE INVENTION

The present invention relates to an organic polymer having a hydrosilyl group, a preparation thereof, and a curable composition comprising said polymer.

BACKGROUND ART

Hitherto, various curable liquid compositions which are cured to give rubbery materials have been developed. Among them, a curing system having good depth curability has been developed, which system is prepared by cross-linking a polyorganosiloxane having on the average two or more vinyl groups at a molecular end or in a molecular chain of one molecule, with a polyorganohydrogensiloxane having two or more hydrogen atoms bonded to silicon atoms in one molecule. Such a system is used as a sealing agent or a potting agent by utilizing its good weather resistance, water resistance and thermal resistance. However, such systems have limited applications because the cost is high, the adhesion property is not good and fungus easily grows. Further, said polyorganosiloxane generally has poor comparability with an organic polymer. When a polyorganohydrogensiloxane and an organic polymer having an alkenyl group are intended to be cured, hydrolysis and dehydrogenation condensation reaction of the polyorganohydrogensiloxane increase due to phase separation, and sufficient mechanical properties are not achieved because of voids.

DISCLOSURE OF THE INVENTION

As the result of an extensive study under such circumstances, the present invention solves these problems. The present invention provides a curable liquid composition having rapid curability, good depth curability and good mechanical properties, an organic polymer having a hydrosilyl group in a molecule which is suitable to give such composition, and preparation of the polymer.

The first aspect of the present invention resides in an organic polymer having at least two hydrosilyl groups in the molecule and having a molecular weight of from 500 to 50,000.

The second aspect of the present invention resides in a method for preparing a hydrosilyl group-containing organic polymer having a molecular weight of from 500 to 50,000 which comprises reacting (A) an organic polymer having at least one alkenyl group in the molecule with (B) a polyvalent hydrogensilicon compound in the presence of a hydrosilylation catalyst so that the hydrosilyl group remains after the reaction.

The third aspect of the present invention resides in a curable composition which comprises (C) an organic polymer having at least two hydrosilyl groups in the molecule, (D) an organic polymer having at least one alkenyl group in the molecule, and (E) a hydrosilylation catalyst.

Polymers having various backbones can be used as the organic polymer having at least two hydrosilyl groups in a molecule and having the molecular weight of from 500 to 50,000 according to the first aspect of the present invention.

For example, a polyether polymer, a polyester polymer, a hydrocarbon polymer, a (meth)acrylate ester polymer and a polycarbonate polymer are mentioned.

Specific examples of the polyether polymer are those having the backbone comprising a repeating unit of, for example,

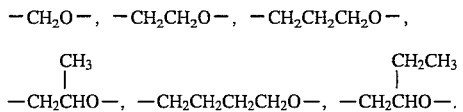

The polyether polymer may comprise one kind of the repeating unit or a combination of two or more kinds of the repeating unit. Specific examples of the polymer are polyoxyethylene, polyoxypropylene, polyoxytetramethylene and polyoxyethylene/polyoxypropylene copolymer. The polyether polymer may be a linear or branched one.

The polyester polymer may have the backbone prepared by, for example, polycondensing a polybasic acid and polyhydric alcohol by a direct esterification, a transesterification or the like. Concretely, the following components may be polycondensed, but the present invention is not restricted to them.

Diol

Ethylene glycol, propylene glycol, butanediol, hexamethylene glycol, hydrogenated bisphenol A, neopentyl glycol, polybutadienediol, diethylene glycol, triethylene glycol and dipropylene glycol Polyol having at least three hydroxyl groups Glycerol, trimethylolmethane, trimethylolpropane and pentaerythritol Dicarboxylic acid Phthalic acid, isophthalic acid, terephthalic acid, tetrahydrophthalic acid, hexahydrophthalic acid, tetrachlorophthalic acid, polybutadiene dicarboxylic acid, oxalic acid, malonic acid, succinic acid, adipic acid, sebacic acid, maleic acid, fumaric acid and cyclopentane dicarboxylic acid Polycarboxylic acid having at least three carboxyl groups Trimellitic acid, butane tricarboxylic acid, pyromellitic acid Further, anhydrides and acyl halides of the above carboxylic acids can be used in addition to these polybasic carboxylic acids.

The backbone of the polyester polymer can be prepared also by a ring opening polymerization of a lactone. Specific examples of the lactone are β-propiolactone, pivalolactone, α-methyl-β-propiolactone, δ-valerolactone, methyl-δ-valerolactone, dimethyl-δ-valerolactone, ε-caprolactone, δ-methyl-ε-caprolactone, dimthyl-ε-caprolactone and the like.

The polyester polymer may be a linear or branched one.

Specific examples of a monomer component constituting the hydrocarbon polymer are olefins having 2 to 12 carbon atoms, acetylene analogues, conjugated dienes, vinyl ethers, aromatic vinyl compounds and the like. Specific examples of the monomer component are ethylene, acetylene, propylene, 1-butene, 2-butene, isobutylene, 2-methyl-1-butene, 3-methyl-1-butene, pentene, pentyne, 4-methyl-1-pentene, hexene, hexyne, vinylcyclohexane, butadiene, isoprene, chloroprene, cyclopentadiene, methyl vinyl ether, ethyl vinyl ether, isobutyl vinyl ether, styrene, α-methylstyrene, dimethylstyrene, monochlorostyrene, dichlorostyrene, β-pinene, indene, cyclopentadiene and the like. Among them, propylene, 1-butene, 2-butene, isobutylene, butadiene, isoprene and the like are preferable. Various hydrocarbon polymers can be prepared from one or at least two of said monomers by a radical polymerization, an ionic polymerization, a coordination ionic polymerization, a living cationic polymerization (so-called Inifer method) which is proposed by Kennedy et al. When dienes and acetylene derivatives are polymerized, double bonds remain in a backbone chain or a side chain after polymerization and subsequently a hydrosilyl group can be introduced by utilizing the double bonds. When the polymer is used in an application requiring a weather resistance, a hydrogenated polymer may be used.

Specific examples of the hydrocarbon polymer are polyisobutylene, ethylene/propylene copolymer, 1,2-polybutadiene, 1,4-polybutadiene, hydrogenated polybutadiene, polyisoprene, hydrogenated polyisoprene and the like, but the hydrocarbon polymer is not restricted to these polymers. The hydrocarbon polymer may be a linear or branched one.

Specific examples of a monomer component constituting the (meth)acrylate ester polymer are acrylic acid and acrylate ester monomers such as methyl acrylate, ethyl acrylate, n-propyl acrylate, isopropyl acrylate, n-butyl acrylate, isobutyl acrylate, sec.-butyl acrylate, tert.-butyl acrylate, 2-ethylhexyl acrylate, lauryl acrylate, tridecyl acrylate, stearyl acrylate, cyclohexyl acrylate, benzyl acrylate, tetrahydrofurfuryl acrylate, 2-hydroxyethyl acrylate, 2-hydroxypropyl acrylate, 2-methoxyethyl acrylate, 2-ethoxyethyl acrylate, 2-butoxyethyl acrylate, 2-phenoxyethyl acrylate, ethyl carbitol acrylate, allyl acrylate, glycidyl acrylate, dimethylaminoethyl acrylate, acrylic acid, sodium acrylate, trimethylolpropane triacrylate, 1,4-butanediol diacrylate, 1,6-hexanediol diacrylate, neopentyl glycol diacrylate and pentaerythritol triacrylate; and methacrylic acid and methacrylate ester monomers such as methyl methacrylate, ethyl methacrylate, butyl methacrylate, isobutyl methacrylate, tert.-butyl methacrylate, 2-ethylhexyl methacrylate, lauryl methacrylate, tridecyl methacrylate, stearyl methacrylate, cyclohexyl methacrylate, propyl methacrylate, benzyl methacrylate, isopropyl methacrylate, sec.-butyl methacrylate, 2-hydroxyethyl methacrylate, 2-hydroxypropyl methacrylate, dimethylaminoethyl methacrylate, diethylaminoethyl methacrylate, glycidyl methacrylate, tetrahydrofurfuryl methacrylate, allyl methacrylate, ethylene glycol methacrylate, triethylene glycol methacrylate, tetraethylene glycol methacrylate, 1,3-butylene glycol methacrylate, trimethylolpropane methacrylate, 2-ethoxyethyl methacrylate, 2-methoxyethyl methacrylate, dimethylaminoethylmethylchloride methacrylate, methacrylic acid and sodium methacrylate. In addition to these (meth)acrylic acid and (meth)acrylate ester monomers, vinyl monomers such as acrylamide, acrylonitrile, vinyl acetate, styrene, ethylene, propylene, isobutylene, butadiene, isoprene and chloroprene can be used as the component of the copolymer.

Various (meth)acrylate ester polymers can be prepared from one or at least two of said monomer components by a radical polymerization, an ionic polymerization, a group transfer polymerization (GTP method) proposed by Du Pont.

The polymer may be a linear or branched one.

Various polycarbonate polymers can be used. The polycarbonate polymer used in the present invention is intended to mean a polymer in which a molecular weight of a dihydroxy compound is increased through at least one carbonate linkage.

The polycarbonate polymer can be prepared by a conventionally used polymerization reaction, for example, (1) a method which comprises reacting a dihydroxy compound with phosgene, (2) a method which comprises a transesterification of an alkylene carbonate and a dihydroxy compound, and (3) a method which comprises a transesterification of a dialkyl carbonate and dihydroxy compound.

Specific examples of the dihydroxy compound which can be used are 1,3-propanediol, 1,4-butanediol, 1,5-pentanediol, 1,6-hexanediol, 1,7-heptanediol, 1,8-octanediol, 2-ethyl-1,6-hexanediol, 2-methyl-1,3-propanediol, neopentyl glycol, 1,3-cyclohexanediol, 1,4-cyclohexanediol, 2,2'-bis(4-hydroxycyclohexyl)-propane, p-xylenediol, p-tetrachloroxylenediol, 1,4-dimethylolcyclohexane, 3(4),8(9)-bis(hydroxymethyl)tricyclodecanedimethylol, bis-hydroxymethyltetrahydrofuran, di(2-hydroxyethyl)dimethylhydantoin, ethylene glycol, diethylene glycol, triethylene glycol, polyethylene glycol, propylene glycol, dipropylene glycol, polypropylene glycol, polytetramethylene glycol,

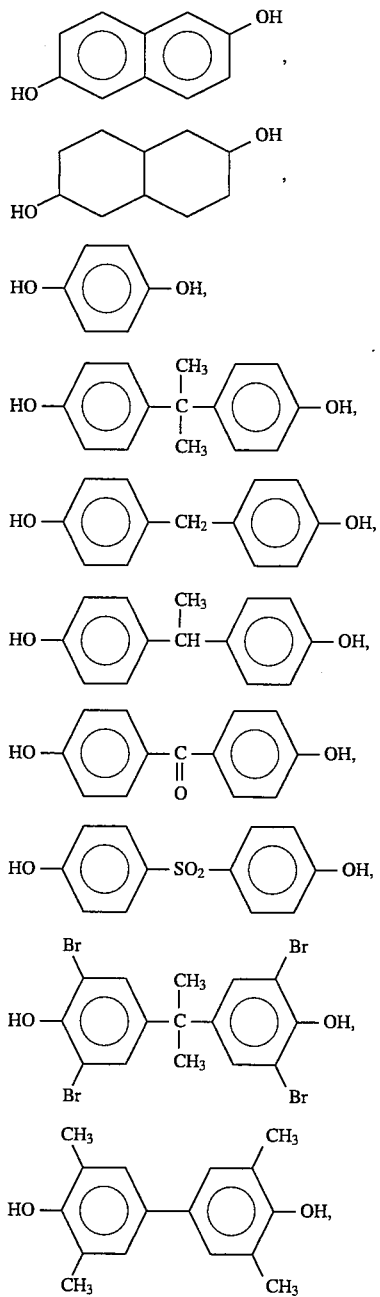

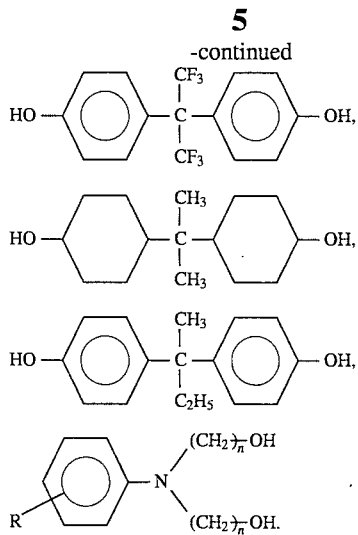

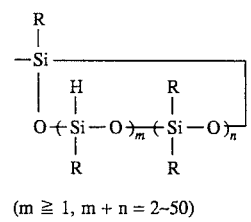

The polycarbonate polymer prepared by using these dihydroxy compounds may be a linear one. Alternatively, the polycarbonate polymer may have branches by, for example, using the polyfunctional hydroxy compound during the polymerization.

The hydrosilyl group contained in the polymer according to the present invention may be in the molecular chain or at the molecular end. When a rubbery cured material is prepared by using the hydrosilyl group-containing organic polymer of the present invention, the hydrosilyl group at the molecular end is preferable since an effective network chain length is elongated.

The hydrosilyl group mentioned in the present invention is generally an arbitrary group which has a Si-H linkage and is not limited. The hydrosilyl group is preferably a group of the formula:

$$X-CH_2CH_2-R^1+O)_a \quad (I)$$

wherein X is a group having at least one hydrosilyl group of the formula:

$(m + n \geq 1, m + n + p + q = 1\text{--}50)$ (wherein each R is, same or different, a group selected from H, $OSi(CH_3)_3$ or an organic group having 1 to 10 carbon atoms.) or

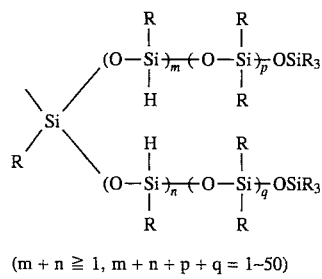

$(m \geq 1, m + n = 2\text{--}50)$ (wherein R is the same as described above.), $R^1$ is a group selected from divalent groups of the formulas:

 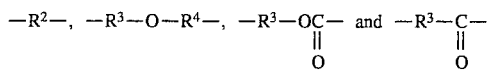

(wherein $R^2$, $R^3$ and $R^4$ are a divalent hydrocarbon group having 1 to 20 carbon atoms.), and a is 0 or 1.

Specific examples of the hydrosilyl group are a hydrosilyl group having only one silicon atom such as $-Si(H)_n(CH_3)_{3-n}$, $-Si(H)_n(C_2H_5)_{3-n}$, $-Si(H)_n(C_6H_5)_{3-n}$ (n=1 to 3), $-SiH_2(C_6H_{13})$;

a hydrosilyl group having at least two silicon atoms such as $-Si(CH_3)_2Si(CH_3)_2H$, $-Si(CH_3)_2CH_2CH_2Si(CH_3)_2H$, $-Si(CH_3)_2Si(CH_3)H_2$,

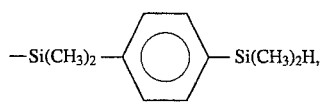

$-Si(CH_3)_2NHSi(CH_3)_2H$, $-Si(CH_3)_2N[Si(CH_3)_2H]_2$,

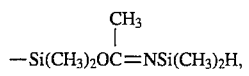

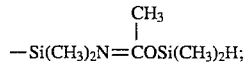

a hydrosilyl group derived from various linear, branched and cyclic polyvalent hydrogensiloxanes of the formula:

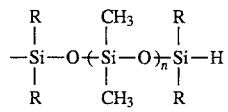

$(R = CH_3, C_2H_5, C_6H_5, OSi(CH_3)_3, n = 0\text{--}50)$

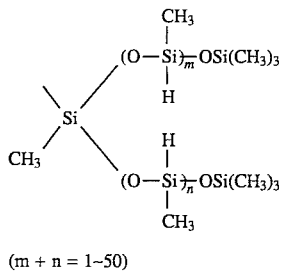

$(m + n = 1\text{--}50)$

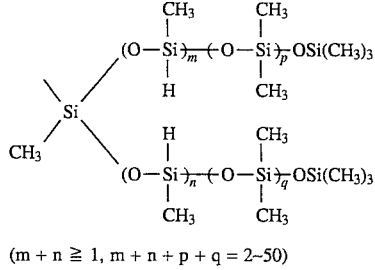

$(m + n \geq 1, m + n + p + q = 2\text{--}50)$

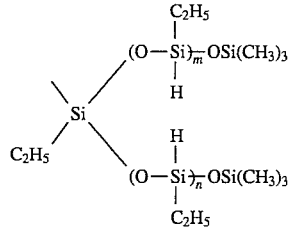

(m + n = 1~50)

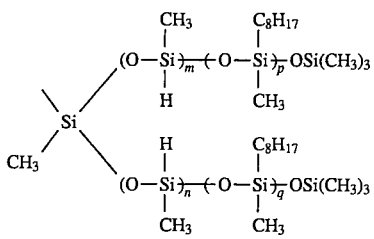

(m + n ≧ 1, m + n + p + q = 2~50)

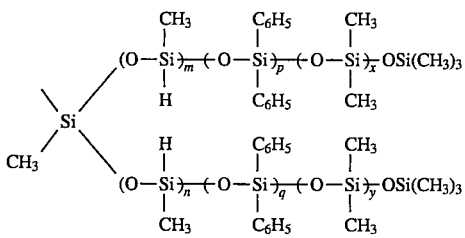

(m + n ≧ 1, m + n + p + q + x + y = 2~50)

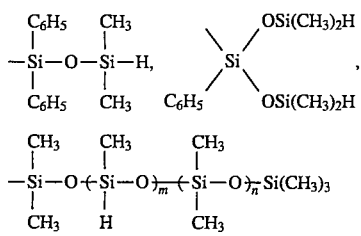

(m + n = 1~50)

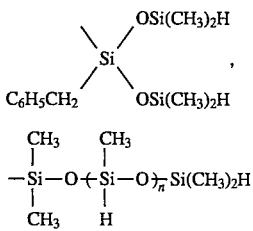

(n = 0~50)

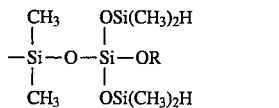

[R = CH$_3$, C$_2$H$_5$, C$_6$H$_5$, Si(CH$_3$)$_3$]

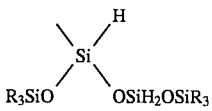

(R = CH$_3$, C$_2$H$_5$, C$_6$H$_5$)

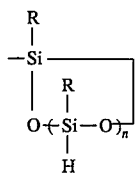

(R = CH$_3$, C$_2$H$_5$, C$_6$H$_5$, n = 1~20)

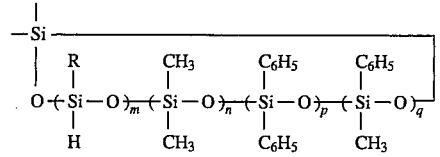

(m ≧ 1, m + n + p + q = 2~20).

Among the above various hydrosilyl groups, the moiety constituting the hydrosilyl group preferably has a molecular weight of lower than 500, since the organic polymer having the hydrosilyl group has a low probability of decreasing the compatibility with various organic polymers. The following is preferable further in view of reactivity of the hydrosilyl group:

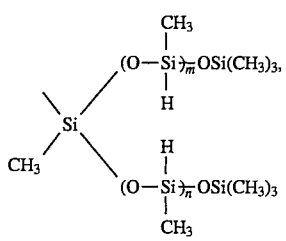

(m + n = 2~4)

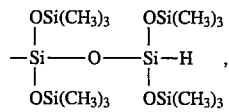

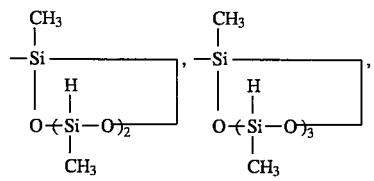

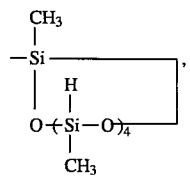

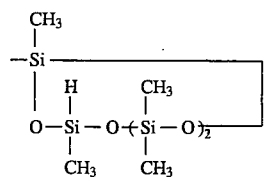

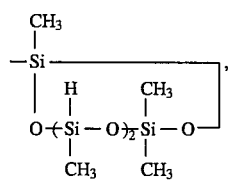

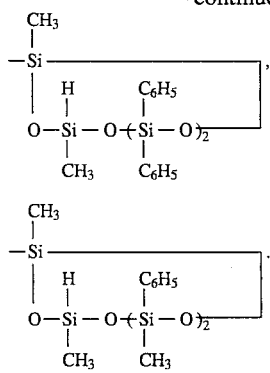

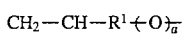

Since the reactivity of the polymer (reactivity of the hydrosilyl group) is high and the compatibility with other polymers is good, a group which has a hydrogen atom bonded to a silicon atom and is based on the cyclic polysiloxane is preferable.

The number of hydrosilyl groups in one molecule is at least 2, preferably 2 to 15, particularly 3 to 12. In the case where the hydrosilyl group-containing organic polymer according to the present invention is mixed with the alkenyl group-containing organic polymer in the presence of the hydrosilylation catalyst, so as to give a cured material through the hydrosilylation reaction, the curing tends to be slow and insufficient if the number of the hydrosilyl groups is smaller than 2. When the number of the hydrosilyl groups is larger than 15, the polymer has bad stability and the cured material has a large number of the hydrosilyl groups after the curing which cause voids and cracking.

The bonding manner of the hydrosilyl group in the hydrosilyl group-containing organic polymer is not limited. The silicon atom may directly bond to the backbone of the organic polymer, or the carbon atom of the carbon-silicon linkage may bond to the backbone of the organic polymer optionally through a urethane, ester, ether or carbonate linkage.

The hydrosilyl group-containing organic polymer according to the present invention preferably has a molecular weight of 500 to 50,000, particularly 500 to 20,000 in view of easy handling, an easy synthesis and compatibility with other polymers.

A method for preparing the hydrosilyl group-containing organic polymer according to the present invention is not limited and is arbitrary. For example, the following methods are contemplated: (i) a method which comprises reducing an Si—Cl group to an Si—H group in an organic polymer having the Si—Cl group in the molecule by treating the organic polymer with a reducing agent such as $LiAlH_4$ or $NaBH_4$, (ii) a method which comprises reacting an organic polymer having a functional group X in the molecule with a compound having hydrosilyl group and a functional group Y which reacts with the functional group X, (iii) a method which comprises retaining a hydrosilyl group in the molecular chain or on the molecular end of an organic polymer after a reaction by selectively hydrosilylating a polyhydrosilane compound having at least two hydrosilyl groups to an organic polymer having an alkenyl group.

The second aspect of the present invention resides in the above method (iii) for preparing the hydrosilyl group-containing organic polymer. Namely, the present invention provides a method for preparing an organic polymer having a hydrosilyl group which comprises reacting (A) an organic polymer having at least one alkenyl group in a molecule with (B) a polyvalent hydrogensilicon compound in the presence of a hydrosilylation catalyst so that the hydrosilyl groups remain after the reaction.

The polymer used as the component (A) is not limited. Various polyether polymers, polyester polymers, hydrocarbon polymers, (meth)acrylate ester polymers and polycarbonate polymers as described above can be used as the component (A).

The alkenyl group is not limited, and is preferably a group of the formula:

$$CH_2=CH-R^1+O\overline{)_a}$$ (II)

wherein $R^1$ is a group selected from divalent organic groups of the formulas:

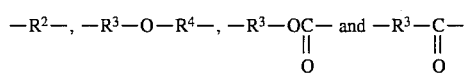

(wherein $R^2$, $R^3$ and $R^4$ are a divalent hydrocarbon group having 1 to 20 carbon atoms.), and a is 0 or 1.

The method of introducing the alkenyl group in the organic polymer is not limited. For example, (i) the alkenyl group can be introduced at the molecular end or in the molecular backbone by reacting an organic polymer having a functional group such as a hydroxy group, an alkoxide group or a carboxyl group with an organic compound having an alkenyl group and an active group which is reactive to said functional group. Specific examples of the organic compound having the alkenyl group and the active group which is reactive to said functional group are a $C_3$–$C_{20}$ unsaturated aliphatic acid, acid halide and acid anhydride such as acrylic acid, methacrylic acid, vinyl acetate, acrylic chloride and acrylic bromide; a $C_3$–$C_{20}$ unsaturated aliphatic acid substituted carbonate halide such as allyl chloroformate ($CH_2$=$CHCH_2OCOCl$) and allyl bromoformate ($CH_2$=$CHCH_2OCOBr$); allyl chloride, allyl bromide, vinyl(chloromethyl)benzene, allyl(chloromethyl)benzene, allyl(bromomethyl)benzene, allyl chloromethyl ether, allyl-(chloromethoxy)benzene, 1-butenyl chloromethyl ether, 1-hexenyl(chloromethoxy)benzene, allyloxy(chloromethyl)benzene and the like.

(ii) In the case of the acrylate ester polymer and the like usually prepared by a radical polymerization, the alkenyl group can be introduced in the polymer molecule by using a monomer component having an alkenyl group with a relatively low radical polymerization property such as allyl acrylate or allyl methacrylate. The alkenyl group can be introduced at the molecular end by using, for radical polymerization, a chain transfer agent having an alkenyl group having a relatively low radical polymerization property such as allyl mercaptan. The alkenyl group can be introduced in a polymer molecule by using, as a monomer component, a monomer having a hydroxy group or a carboxyl group such as 2-hydroxylethyl methacrylate or acrylic acid to carry out a polymerization, and then reacting the polymer with an organic compound having an alkenyl group and a functional group which is reactive to said functional group. Specific examples of the organic compound having the alkenyl group and the functional group which is reactive to said functional group are compounds described in method (i).

(iii) When a diene or acetylene monomer component is used for the preparation of the hydrocarbon polymer, a double bond which remains after polymerization can be used as the alkenyl group.

The alkenyl group of the organic polymer (A) may be present at the molecular end or in the molecular chain. When a rubbery cured material is prepared by using the hydrosilyl group-containing organic polymer, the alkenyl group at the molecular end is preferable since the hydrosilyl group can be introduced on the molecular end and an effective network chain length of the cured material is elongated.

The number of the alkenyl groups in one molecule is at least one, preferably 2 to 6.

Specific examples of the polyvalent hydrogensilicon compound (B) used according to the present invention are a monosilane compound such as $(CH_3)_2SiH_2$, $(C_6H_5)_2SiH_2$, $CH_3SiH_3$, $C_6H_5SiH_3$, $(C_2H_5)_2SiH_2$ and $CH_3(CH_2)_5SiH_3$; a polysilicon compound such as $H(CH_3)_2SiSi(CH_3)_2H$, $H(CH_3)_2SiCH_2CH_2Si(CH_3)_2H$,

$H(CH_3)_2SiSi(CH_3)H_2$, $H(CH_3)_2Si\ NHSi(CH_3)_2H$, $[H(CH_3)_2Si]_3N$ and $H(CH_3)_2SiOC(CH_3)=NSi(CH_3)_2H$; and various linear, branched and cyclic polyvalent hydrogen polysiloxane such as

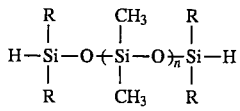

($R = CH_3, C_6H_5, C_2H_5, OSi(CH_3)_3$) ($n = 0\text{--}50$),

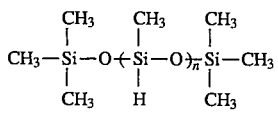

($n = 2\text{--}50$),

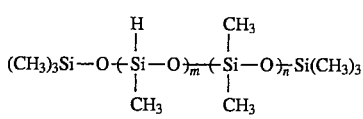

($n \geq 2$, $m + n = 2\text{--}50$),

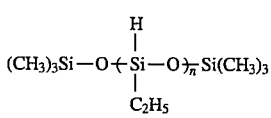

($n = 2\text{--}50$),

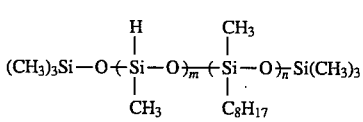

($m \geq 2$, $m + n = 3\text{--}50$),

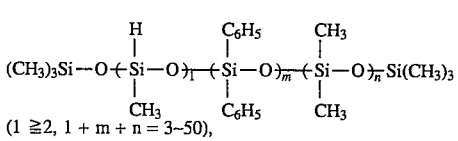

($1 \geq 2$, $l + m + n = 3\text{--}50$),

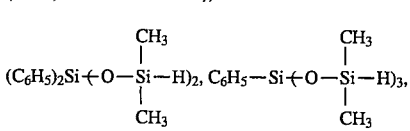

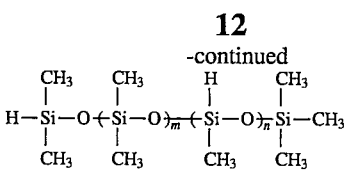

($n \geq 2$, $m + n = 3\text{--}50$),

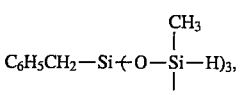

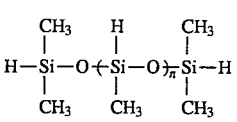

($2 \leq n \leq 50$),

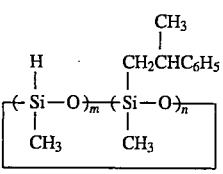

($m + n = 3\text{--}6$, $m \geq 2$), $RSi[OSi(CH_3)_2H]_3$ ($R = CH_3, C_6H_5, C_2H_5$), $Si[OSi(CH_3)_2H]_4$

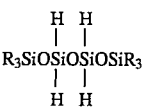

($R = CH_3, C_6H_5, C_2H_5$),

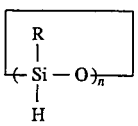

($n = 3\text{--}20$) ($R = CH_3, C_6H_5, C_2H_5$),

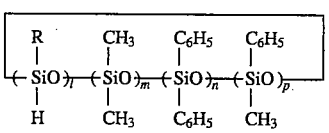

($1 \geq 2$, $p + 1 + m + n = 3\text{--}20$ $R = CH_3, C_2H_5, C_6H_5$).

The number of hydrosilyl groups in one molecule of the polyvalent hydrogensilicon compound (B) is preferably 3 to 16, particularly 4 to 13. Since the hydrosilyl group-containing organic polymer according to the present invention prepared from the component (A) and the component (B) does not deteriorate poor compatibility, the polyvalent hydrogensilicon compound (B) preferably has a molecular weight of lower than 500. Since a hydrosilylating reaction of the component (A) and component (B) has high reactivity, the following compounds are preferable:

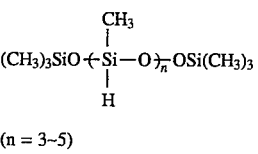

($n = 3\text{--}5$)

-continued

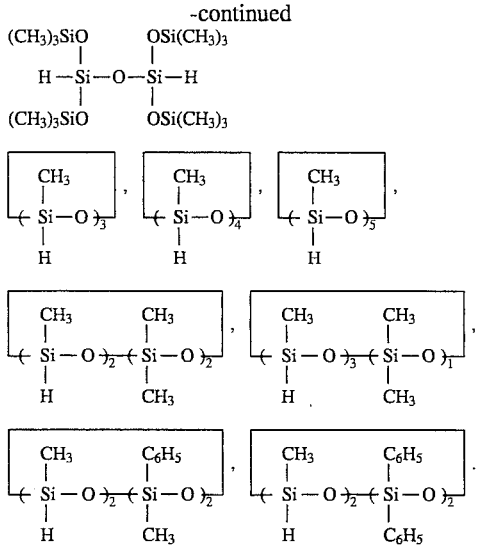

Since the compatibility with the alkenyl-group containing organic polymer is generally good, the reactivity with the alkenyl group in the organic polymer is high and unreacted components can be easily removed under a reduced pressure after hydrosilylating reaction. The following compounds are particularly preferable:

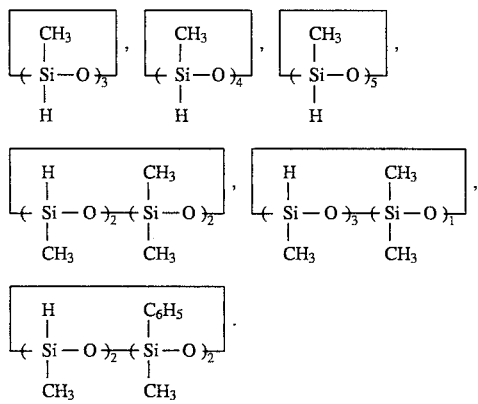

The hydrosilyl group-containing organic polymer according to the present invention can be prepared by the hydrosilylation reaction of the alkenyl group-containing organic polymer (A) and the polyvalent hydrogensilicon compound (B). Specific examples of a catalyst used for the reaction are platinum as such; solid platinum supported on a carrier such as alumina, silica or carbon black; chloroplatinic acid; a complex of chloroplatinic acid with an alcohol, an aldehyde or a ketone; a platinum-olefin complex (for example, $Pt(CH_2=CH_2)_2(PPh_3)_2Pt(CH_2=CH_2)_2Cl$); a platinum-vinylsiloxane complex (for example, $Pt_n(ViMe_2SiOSiMe_2Vi)_m$, $Pt[(MeViSiO)_4]_m$); a platinum-phosphine complex (for example, $Pt(PPh_3)_4, Pt(PBu_3)_4$); a platinum-phosphite complex (for example, $Pt[P(OPh)_3]_4$, $Pt[P(OBu)_3]_4$) (wherein Me is a methyl group, Bu is a butyl group, Vi is a vinyl group, Ph is a phenyl group, and n and m are an integer.); dicarbonyldichloroplatinum; a platinum-hydrocarbon complex described in U.S. Pat. Nos. 3,159,601 and 3,159,662 to Ashby; and a platinum alcoholate catalyst described in U.S. Pat. No. 3,220,972 to Lamoreaux. In addition, a platinum chloride-olefin complex described in U.S. Pat. No. 3,516,946 to Modic is also useful in the present invention.

Specific examples of the catalyst other than the platinum compounds are $RhCl(PPh_3)_3, RhCl_3, Rh/Al_2O_3, RuCl_3, IrCl_3$, $FeCl_3, AlCl_3, PdCl_2 \cdot 2H_2O, NiCl_2$ and $TiCl_4$ (Ph is a phenyl group.). Only one catalyst or a combination of at least two catalysts may be used. In view of catalytic activity, chloroplatinic acid, the platinum-olefin complex, the platinum-vinylsiloxane complex and the like are preferable. An amount of the catalyst is not limited, but $10^{-1}$ to $10^{-8}$ mol, based on the alkenyl group of the component (A), may be used. The range between $10^{-3}$ and $10^{-6}$ mol is preferable.

The use of a solvent is not necessarily required in the hydrosilylating reaction. An inert organic solvent may be used when the starting materials have a high viscosity and it is difficult to carry out an operation such as a stirring. Specific examples of the inert organic solvent are aromatic hydrocarbon solvents such as benzene, toluene and xylene; aliphatic hydrocarbon solvents such as hexane and octane; ether solvents such as ethyl ether and butyl ether; ketone solvents such as methyl ethyl ketone; halogenated hydrocarbon solvents such as trichloroethylene.

The manner for adding the component (A), the component (B) and the hydrosilylation catalyst is not limited and includes charging three components simultaneously, adding the component (A) and the hydrosilylation catalyst to the component (B), adding the component (B) to the component (A) and the hydrosilylation catalyst, adding the component (A) to the component (B) and the catalyst, and adding each component simultaneously. In order to carry out the reaction so that the hydrosilyl group remains after the reaction, preferably the polyvalent hydrogensilicon compound is always present in excess to the component (A). Therefore, it is preferable to add a mixture of the alkenyl group-containing organic polymer (A) and the hydrosilylation catalyst to the polyvalent hydrogensilicon compound (B). The reaction temperature may be from 0° to 200° C., preferably from 50° to 150° C. When the reaction temperature is lower than 0° C., the catalyst activity is insufficient and therefore the reaction rate is low. When it is higher than 200° C., the catalyst is often deactivated.

In the hydrosilylating reaction according to the present invention, under any reaction conditions, at least two hydrosilyl groups of a part of polyvalent hydrogensilicon compound react with the alkenyl groups of the component (A) and a phenomenon such as the viscosity increase caused by the molecular weight increase is sometimes observed.

Since the hydrosilyl group-containing organic polymer prepared by the above method usually contains the hydrosilylating catalyst after the reaction, its stability is generally poor. When the organic polymer is kept standing for a long time or exposed to the moisture, an Si—H group converts to an Si—OH group and a phenomenon such as the viscosity increase or the gelation is observed. Therefore, the catalyst is preferably removed from the polymer after the hydrosilylating reaction. Specific examples for a method for removing the catalyst are a method which comprises mixing a reaction solution after the polymerization with silica, silica gel, an ion exchange resin or the like or treating the reaction solution with a column comprising the same, and a method which comprises washing a reaction mixture with a neutral or weakly acidic aqueous solution.

The hydrosilyl group-containing organic polymer prepared in this manner generally has better compatibility with an organic polymer, particularly of the same kind, in comparison with known hydrosilyl group-containing polysiloxanes. When the hydrosilyl group-containing organic polymer according to the present invention is mixed with the alkenyl group-containing organic polymer in the presence of said various hydrosilylation catalysts and then cured, a homogeneous cured material can be obtained without a phenomenon such as foaming since these polymers have good compatibility. The curing conditions are not limited. In general, the curing can be carried out at 0° to 200° C., preferably 50° to 150° C. for 10 seconds to 4 hours. At a high temperature of 80° to 150° C., the curing is sometimes completed after a short time of 10 seconds to 30 minutes. For example, even if the cured material prepared according to said method has a thickness of at least 1 cm, the homogeneously cured material having good depth curability can be obtained. Properties of the cured material depend on the backbone and the molecular weight of the organic polymers and the like. A rubbery material to a resinous material can be prepared.

When the cured material is prepared, various solvents, plasticizers, fillers, pot-life extending agents, pigments, age resistors, ultraviolet light absorbers and adhesives can be used in addition to three main components of the hydrosilylation catalyst, the hydrosilyl group-containing organic polymer and the alkenyl group-containing organic polymer.

The third aspect of the present invention resides in a curable composition which comprises (C) an organic polymer having at least two hydrosilyl groups in a molecule, (D) an organic polymer having at least one alkenyl group in a molecule, and (E) a hydrosilylation catalyst.

Various hydrosilyl group-containing polyether, polyester, hydrocarbon, (meth)acrylate ester and polycarbonate polymers which are described in connection with the first aspect can be used as the organic polymer (C) having at least two hydrosilyl groups. Preferable molecular weight and backbone of said polymer, preferable structure of the hydrosilyl group, preferable number of the hydrosilyl groups per one molecule and preferable linkage site to backbone of the hydrosilyl group are the same as those made in the explanation of the first aspect. A method for preparing the component (C) is not limited, but the method of the second aspect is preferable.

Various alkenyl group-containing organic polymers such as the polyether, polyester, hydrocarbon, acrylate ester and polycarbonate which are the component (A) described in connection with the second aspect can be used as the organic polymer (D) having at least one alkenyl group.

Other examples of the polymer are a copolymer of isobutylene with isoprene or the like; polychloroprene; polyisoprene; a copolymer of isoprene with butadiene, acrylonitrile, styrene or the like; polybutadiene; a copolymer of butadiene with styrene, acrylonitrile or the like; a polyolefin polymer prepared by hydrogenating polyisoprene, polybutadiene, or a copolymer of isoprene or butadiene with acrylonitrile, styrene or the like; an acrylate ester copolymer of an acrylate ester such as ethyl acrylate or butyl acrylate with vinyl acetate, acrylonitrile, methyl methacrylate, styrene or the like; a graft polymer prepared by polymerizing a vinyl monomer in said organic polymer; polysulfide polymer; nylon 6 prepared by a ring opening polymerization of ε-aminocaprolactam; nylon 66 prepared by a polycondensation of hexamethylene-diamine and adipic acid; nylon 610 prepared by a polycondensation of hexamethylenediamine and sebacic acid; nylon 11 prepared by a polycondensation of ε-aminoundecanoic acid; nylon 12 prepared by a ring opening polymerization of ε-aminolauric lactam; a polyamide polymer such as copolymerized nylon containing at least two components of said nylon; and a diallyl phthalate polymer.

Among the polymers having the above backbones, the polyether polymer, the (meth)acrylate ester polymer, the (meth)acrylate ester copolymer, the hydrocarbon polymer and the polyester polymer are preferable since they have good compatibility with the hydrosilyl group-containing organic polymer (C). In particular, combinations in which both of the components (C) and (D) are the polyether polymer, the polyester polymer, the hydrocarbon polymer or the (meth)acrylate ester polymer are preferable.

The alkenyl group is not limited and the preferable alkenyl group is of the formula:

$$CH_2=C-R^1-(O)_{\overline{a}} \quad (III)$$
$$\quad\ |$$
$$\quad R^5$$

wherein $R^1$ is a group selected from divalent organic groups of the formulas:

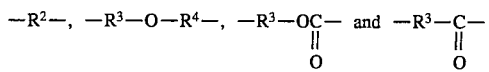

(wherein $R^2$, $R^3$ and $R^4$ are a divalent hydrocarbon group having 1 to 20 carbon atoms.), $R^5$ is hydrogen or a methyl group, and $a$ is an integer of 0 or 1.

A method for introducing the alkenyl group into the organic polymer (D) may be a conventionally proposed method and is roughly classified in a method for introducing the alkenyl group after the polymerization and a method for introducing the alkenyl group during the polymerization.

The method for introducing the alkenyl group after the polymerization includes, for example, a method comprising reacting an organic polymer having a functional group such as a hydroxy group, an alkoxide group or a carboxyl group at the molecular end, in the backbone or in the side chain, with an organic compound having an alkenyl group and an active group which is reactive to said functional group so as to introduce the alkenyl group at the molecular end, in the backbone or in the side chain. Specific examples of the organic compound having the alkenyl group and the active group which is reactive to said functional group are a $C_3$–$C_{20}$ unsaturated aliphatic acid, acid halide and acid anhydride such as acrylic acid, methacrylic acid, vinyl acetate, acrylic chloride and acrylic bromide; a $C_3$–$C_{20}$ unsaturated aliphatic acid substituted carbonate halide such as allyl chloroformate ($CH_2=CHCH_2OCOCl$) and allyl bromoformate ($CH_2=CHCH_2OCOBr$); allyl chloride, allyl bromide, vinyl(chloromethyl)benzene, allyl(chloromethyl)benzene, allyl(bromomethyl)benzene, allyl chloromethyl ether, allyl(chloromethoxy)benzene, 1-butenyl chloromethyl ether, 1-hexenyl(chloromethoxy)benzene and allyloxy(chloromethyl)benzene.

The method for introducing the alkenyl group during the polymerization includes, for example, a method comprising introducing the alkenyl group in the backbone or at the molecular end of the polymer by using a vinyl monomer which has an alkenyl group having a low radical reactivity in the molecule such as allyl methacrylate and allyl acrylate, or a radical chain transfer agent which has an alkenyl group having a low radical reactivity such as allyl mercaptan when the organic polymer (D) is prepared by a radical polymerization.

The molecular weight of the component (D) is preferably from 500 to 50,000, more preferably from 500 to 20,000 in view of the properties of the cured material and the compatibility with the component (C). The number of the alkenyl groups present in one molecule is preferably from 1 to 10, particularly from 2 to 5. When a rubbery cured material is prepared from components (C), (D) and (E), the alkenyl group of the component (D) is preferably present on the molecular end since the effective network chain length of the cured material is elongated.

The molar ratio of the hydrosilyl group to the alkenyl group in the components (C) and (D) is preferably from 0.2 to 5.0, more preferably from 0.4 to 2.5. When the molar ratio is smaller than 0.2, the curing is insufficient and only a sticky cured material having low strength is obtained. When the molar ratio is larger than 5.0, the cracking and voids occur and a homogeneous cured material having high strength cannot be obtained since many active hydrosilyl groups remain in the cured material after the curing.

The hydrosilylation catalyst (E) according to the present invention is not limited and is arbitrary.

Concretely, the same catalyst as used in the preparation of the hydrosilyl group-containing organic polymer according to the second aspect of the present invention can be used. One of these catalysts may be used or a combination of at least two of these catalysts may be used. Chloroplatinic acid, platinum-olefin complex and platinum-vinylsiloxane complex are preferable in view of the catalyst activity. A catalyst amount is not limited, but it is preferably from $10^{-1}$ to $10^{-8}$ mol based on 1 mol of the alkenyl group of the component (D). $10^{-3}$ to $10^{-6}$ mol is more preferable.

The homogeneous cured material having good depth curability without a phenomenon such as the foaming can be obtained by mixing the components (C), (D) and (E) and effecting the curing. Curing conditions are not limited, but the curing is generally carried out at 0° to 200° C., preferably 30 to 150° C. for 10 seconds to 4 hours. In particular, at a high temperature of 80° to 150° C., the curing is sometimes completed after a short time of 10 seconds to 1 hour. Properties of the cured material depend on the backbone and the molecular weight of the polymers (C) and (D), and a rubbery material to a resinous material can be prepared.

When the cured material is prepared, various solvents, adhesion improving agents, property controlling agents, preservation stability improving agents, plasticizers, fillers, age resistors, ultraviolet light absorbers, metal inactivating agents, antiozonants, light stabilizers, amine-based radical chain inhibiting agents, phosphorus-based peroxide decomposers, lubricants, pigments, foaming agents and the like can suitably be added according to the desired application in addition to the three essential components (C), (D) and (E).

When the composition according to the present invention is used, a homogeneous organic cured material having good mechanical properties, high curing speed and good depth curability.

EXAMPLES

The present invention is explained with referring the Examples, but it is not limited to the Examples.

Preparative Example 1

Polyoxypropylene having an allyl-type olefin group at a molecular end was prepared according to a method disclosed in Japanese Patent Kokai Publication No. 134095/1978. Polyoxypropylene glycol having an average molecular weight of 3,000 and sodium hydroxide powder were stirred at 60° C., and bromochloromethane was added to carry out the reaction and increase the molecular weight. Then, allyl chloride was added to etherify the molecular end with the allyl group at 110° C. This was treated with aluminum silicate and purified to prepare allyl ether-terminated polyoxypropylene.

This polyether had an average molecular weight of 7,960 and 92% of the terminal groups were olefin groups according to the iodine value. A viscosity measured by an E-type viscometer was 130 poises (40° C). For reference, 300 MHz NMR spectra of resulted ally ether-terminated polypropylene oxide are shown in FIGS. 1 to 3.

Preparative Example 2

In a round-bottom flask equipped with a stirring rod, a thermometer, a dropping funnel, a nitrogen introducing tube and a condenser, 300 g (0.1 mol) of hydroxy group-terminated polycaprolactone (a number average molecular weight: 3,000, a hydroxy group equivalent: 1,500), 24.0 g of pyridine, and 300 ml of THF were charged. 32 Grams of allyl chloroformate was slowly dropwise added from the dropping funnel at a room temperature. Then, the mixture was heated to 50° C. and stirred for 3 hours. After a resulting salt was removed by filtration, 150 ml of toluene was added and the mixture was washed with 200 ml of aqueous hydrochloric acid and neutralized and condensed to obtain allyl-terminated polycaprolactone. The resulting oligomer had a number average molecular weight of 3,200 according to a VPO measurement. A 300 MHz NMR of an olefin portion confirmed the introduction of the allyl group. The quantification of the olefin by an iodometric titration confirmed that the number of allyl-type unsaturated groups introduced in one molecule was 2.0 on the average.

Preparative Example 3

To 300 g of hydrogenated polyisoprene having a hydroxy group at both ends (Epol (trade name) manufactured by Idemitsu Sekiyu Kagaku Kabushiki Kaisha), 50 ml of toluene was added and the dehydration was carried out with azeotropy. A solution of t-BuOK (48 g) in THF (200 ml) was injected. After the reaction was carried out at 50° C. for 1 hour, 47 ml of allyl chloride was dropwise added over about 30 minutes. After the addition was completed, the reaction was carried out at 50° C. for 1 hour. After the reaction was completed, 30 g of aluminum silicate was added to the reaction solution so as to absorb a resulting salt and then the mixture was stirred at a room temperature for 30 minutes. Through filtration and purification, about 250 g of allyl-terminated hydrogenated polyisoprene was obtained as a viscous liquid. A 300 MHz $^1$H-NMR analysis confirmed that the allyl group was introduced at 92% of the ends. The molar number of the olefin determined according to the iodine value was 0.1072 mol/100 g. A viscosity according to an E-type viscometer was 302 poises (23° C.).

Typical properties of Epol (from a technical brochure)

| | |
|---|---|
| Hydroxy group content (meq/g) | 0.90 |
| Viscosity (poise/30° C.) | 700 |
| Average molecular weight (measured by VPO) | 2,500 |

Preparative Example 4

An agitating blade, a three-way cock and a vacuum line were attached to a one liter pressure-resistant glass autoclave, and the polymerization vessel was dried by heating it at 100° C. for one hour while evacuating through the vacuum line. After cooling it to a room temperature, a nitrogen gas was introduced to reach an atmospheric pressure by means of the three-way cock.

Then, 400 ml of 1,1-dichloroethane (main solvent) dried by a calcium hydride treatment was introduced in the autoclave from one inlet of the three-way cock by means of an injector while flowing the nitrogen gas. 200 ml of nitroethane (additional solvent) dried by a calcium chloride treatment was introduced and then a solution of TCC (20 mmol, tricumyl chloride:

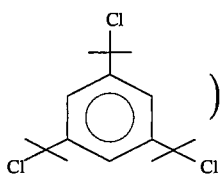

in 1,1-dichloroethane (100 ml) was added.

Subsequently, a pressure-resistant glass-made liquefied gas sampling tube equipped with a needle valve which contained 70 g of isobutylene dehydrated by passing through a column filled with barium oxide was connected with the three-way cock, and then the vessel was immersed in a dry ice-acetone bath at a temperature of $-70°$ C. and the content of the polymerization vessel was cooled for 1 hour while stirring. After cooling, the internal space of the vessel is evacuated through the vacuum line, and then the needle valve was opened to introduce isobutylene in the polymerization vessel from the pressure-resistant glass-made liquefied gas sampling tube. Then, the internal space was returned to an atmospheric pressure by flowing the nitrogen gas from one outlet of the three-way cock, the cooling was kept for 1 hour with stirring and the content in the vessel was cooled to $-60°$ C.

Then, 32 g (100 mmol) of $TiCl_4$ was added through the three-way cock by means of an injector to initiate the polymerization, and, after 60 minutes, 100 mmol of allyltrimethylsilane previously cooled to below 0° C. was added. Then, the temperature was gradually raised to a room temperature while stirring and the reaction was completed by adding methanol.

Then, the reaction mixture was transferred to an egg-plant type flask, and unreacted isobutylene, 1,1-dichloroethane, nitroethane, allyltrimethylsilane and methanol were distilled off. After a remaining polymer was dissolved in 500 ml of n-hexane, the washing of the solution with water was repeated until this solution become neutral. Then, an n-hexane solution was concentrated to 200 ml and the concentrated solution was poured in 2 liters of acetone to precipitate the polymer.

The obtained polymer was dissolved again in 500 ml of n-hexane, and the solution was dried with anhydrous magnesium sulfate and filtered. n-Hexane was distilled off under vacuum to obtain an allyl group-terminated isobutylene polymer.

The yield was calculated from an amount of the obtained polymer. $\overline{Mn}$ and $\overline{Mn}$ were determined by a GPC method. The terminal structure was determined by measuring and comparing the strength of resonance signal of proton assigned to each structure by means of $^1$H-NMR (300 MHz).

Yield: 90 % (65 g)

$\overline{Mn}=3,800$, $\overline{Mw}/\overline{Mn}=1.20$

The number of allyl groups per one molecule≅3.0

Preparative Example 5

A one liter four-necked flask equipped with a stirring rod, a dropping funnel, a thermometer, a three-way cock and a condenser was used. In the flask, 20 ml of toluene was charged under a nitrogen atmosphere. A monomer solution in toluene consisting of 25.6 g of n-butyl acrylate, 2.52 g of allyl methacrylate, 0.81 g of n-dodecyl mercaptan, 1.0 g of azobisisobutyronitrile and 100 ml of toluene was dropwise added over about one hour from the dropping funnel while refluxing toluene. After the addition was completed, the reaction was continued for 2 hours. After the toluene solution was treated with aluminum silicate, it was filtered with suction by using a filtering aid (diatomaceous earth) to give a substantially transparent solution. The solution was evaporated and further dried under a reduced pressure at 80° C. for 3 hours to give about 26 g of a pale yellow viscous liquid oligomer. A molar number of the allyl group in the polymer was 0.154 mol/100 g according to the iodometric titration. A molecular weight was 3,900 according to a VPO. The molecular weight and the molar number of the allyl group according to the iodometric titration revealed that about 6 allyl groups on the average were introduced in one molecule of the polymer.

Example 1

A one liter four-necked flask equipped with a stirring rod, a dropping funnel, a thermometer, a three-way cock and a condenser was used. In the flask, 41.7 g (0.173 mol) of a cyclic polysiloxane:

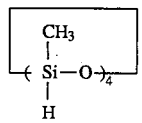

(LS 8600 manufactured by Shin-Etsu Chemical Co., Ltd.) was charged under a nitrogen atmosphere. A toluene solution consisting of 300 g of polypropylene oxide prepared in Preparative Example 1 in which 92% of the molecular ends have the allyl group (molar number of the allyl group: 0.069 mol), 230 ml of toluene and 83 µl of a solution of chloroplatinic acid catalyst (a solution in which $H_2PtCl_6 \cdot 6H_2O$ (1 g) is dissolved in ethanol (1 ml) and 1,2-dimethoxyethane (9 ml)) was charged in the dropping funnel. The flask was heated to 70° C. and the toluene solution was dropwise added over 5 hours at the rate of 2 ml per one minute. Then, the reaction temperature was raised to 80° C. After the stirring was continued for 6 hours, the remaining allyl group in the reaction solution was determined by IR spectra analysis. The disappearance of the carbon-carbon double bond peak at 1645 cm$^{-1}$ was confirmed. Further, for removing toluene and unreacted excessive cyclic polysiloxane in the reaction system, the vacuum degassing was carried out at 80° C. for 3 hours to give about 315 g of polypropylene oxide having the hydrosilyl group as a pale yellow viscous liquid. The viscosity was 310 poises (40° C.) according to an E-type viscometer. The hydrosilyl group in the polypropylene was confirmed as a strong peak of 2150 cm$^{-1}$ in the IR spectra. FIGS. 4 to 7 show 300 MHz NMR spectra. The peak of the allyl group observed in FIGS. 1 to 3 disappeared and an absorption based on Si—$\underline{CH_3}$ around 0.17 to 0.25 ppm and an absorption based on Si—$\underline{H}$ around 4.66 to 4.76 ppm newly appeared (FIGS. 4 to 7). Further, a triplet absorption based on Si—$\underline{CH_2}$—$\underline{CH_2}$—$\underline{CH_2}$—O— was observed at 0.134 ppm, and this indicates that a new Si—C linkage formed through a hydrosilylation reaction.

By comparing the peak intensity of combined Si—$\underline{CH_3}$ and Si$\underline{CH_2}$— with that of the Si—$\underline{H}$, it was revealed that 1.31 hydrosilyl groups on the average per one molecule of said cyclic polysiloxane had been consumed (cf. FIGS. 5 and 6 and the explanation of the drawings). Namely, the polymer is polypropylene oxide having an increased molecular weight because of cyclic hydrogenpolysiloxane and having the following molecular end:

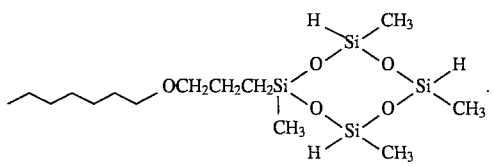

Example 2

The reaction was carried out in the same manner as in Example 1 except that 52.1 g (0.173 mol) of a cyclic polysiloxane:

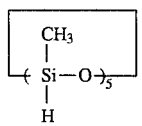

(LS 8990 manufactured by Shin-Etsu Chemical Co., Ltd.) was used. 318 Grams of pale yellow viscous polypropylene oxide having the hydrosilyl group was obtained. A viscosity was 380 poises (40° C.) according to an E-type viscometer. NMR spectra revealed that 1.35 hydrosilyl groups on the average per one molecule of said cyclic polysiloxane had been consumed. Namely, the polymer is a polypropylene oxide having an increased molecular weight because of cyclic hydrogenpolysiloxane and having the following molecular end:

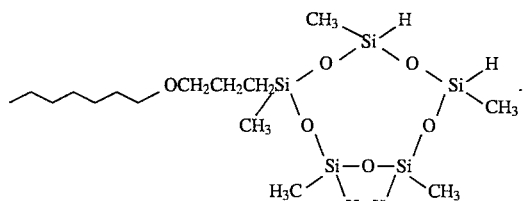

Example 3

A 300 ml four-necked flask equipped with a stirring rod, a dropping funnel, a thermometer, a three-way cock and a condenser was used. In the flask, 34.55 g (0.1435 mol) of a cyclic polysiloxane:

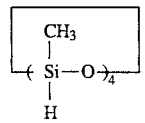

(LS 8600 manufactured by Shin-Etsu Chemical Co., Ltd.) was charged under a nitrogen atmosphere. A toluene solution consisting of 100 g of polycaprolactone prepared in Preparative Example 2 which has 2.0 allyl groups on the average in one molecule (molar number of the olefin: 0.0575 mol), 100 ml of toluene and 60 μl of a solution of chloroplatinic acid catalyst (a solution in which $H_2PtCl_6 \cdot 6H_2O$ (1 g) is dissolved in ethanol (1 ml) and 1,2-dimethoxyethane (9 ml)) was charged in the dropping funnel. The flask was heated to 70° C. and the toluene solution was dropwise added over 2 hours. After the addition was completed and the stirring was continued at 80° C. for 5 hours, the remaining allyl group in the reaction solution was determined by IR spectra analysis. The disappearance of carbon-carbon double bond peak at 1645 cm$^{-1}$ was confirmed. Then, for removal of the catalyst remaining in the reaction system, 10 g of silica gel (Wakogel C-200 manufactured by Wako Junyaku Kabushiki Kaisha) was added at room temperature and the mixture was stirred for 2 hours and filtered with a flash column. For removing toluene and unreacted excessive cyclic polysiloxane, the filtrate was evaporated and the degassing under vacuum was carried out at 80° C. for 3 hours to give a colorless transparent viscous liquid. The hydrosilyl group in polycaprolactone was confirmed as the strong peak of 2150 cm$^{-1}$ according to the IR spectra. By comparing the peak intensity of combined Si—C$\underline{H}_3$ and SiC$\underline{H}_2$— with that of the Si—$\underline{H}$ in 300 MHz NMR spectra, it was revealed that 1.05 hydrosilyl groups on the average per one molecule of said cyclic polysiloxane had been consumed. Namely, the polymer is a polycaprolactone having an increased molecular weight because of cyclic hydrogenpolysiloxane and having the following molecular end:

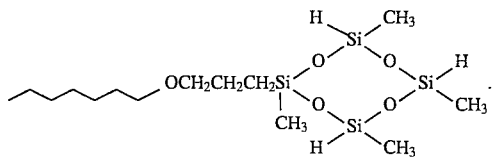

Example 4

A 300 ml four-necked flask equipped with a stirring rod, a dropping funnel, a thermometer, a three-way cock and a condenser was used. In the flask, 31.5 g (0.131 mol) of a cyclic polysiloxane:

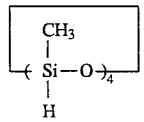

(LS 8600 manufactured by Shin-Etsu Chemical Co., Ltd.) was charged under a nitrogen atmosphere. A toluene solution consisting of 50 g of hydrogenated polyisoprene prepared in Preparative Example 3 in which 92% of molecular ends have allyl group (molar number of the olefin: 0.0536 mol), 50 ml of toluene and 60 μl of a solution of chloroplatinic acid catalyst (a solution in which $H_2PtCl_6 \cdot 6H_2O$ (1 g) is dissolved in ethanol (1 ml) and 1,2-dimethoxyethane (9 ml))

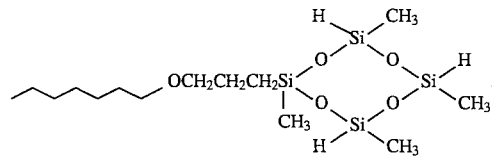

Example 5

A 300 ml four-necked flask equipped with a stirring rod, a dropping funnel, a thermometer, a three-way cock and a condenser was used. In the flask, 20.0 g (0.083 mol) of a cyclic polysiloxane:

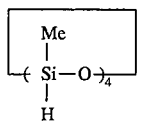

(LS 8600 manufactured by Shin-Etsu Chemical Co., Ltd.) was charged under a nitrogen atmosphere. A toluene solution

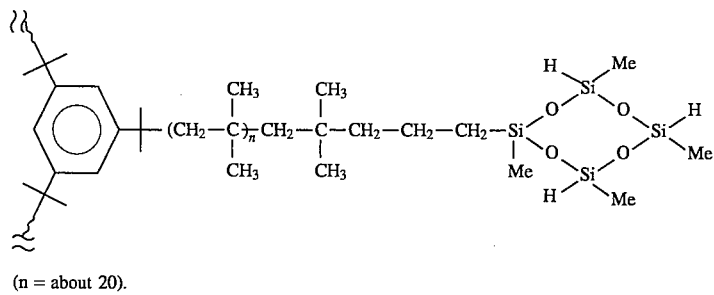

(n = about 20).

consisting of 38 g of polyisobutylene prepared in Preparative Example 4 which has three allyl end groups per one molecule (molar number of the olefin: 0.003 mol), 100 ml of toluene and 50 μl of a solution of chloroplatinic acid catalyst (the same as in Preparative Example 2) was charged in the dropping funnel. The flask was heated to 70° C. and the toluene solution was dropwise added over 3 hours. After the addition was completed and the stirring was continued at was charged in the dropping funnel. The flask was heated to 70° C. and the toluene solution was dropwise added over 2 hours. After the addition was completed and the stirring was continued at 80° C. for 5 hours, the remaining allyl group in the reaction solution was determined by IR spectra analysis. The disappearance of carbon-carbon double bond peak at 1645 cm$^{-1}$ was confirmed. Then, for removal of the catalyst remaining in the reaction system, 5 g of silica gel (Wakogel C-200 manufactured by Wako Junyaku Kabushiki Kaisha) was added at room temperature and the mixture was stirred for 2 hours and filtered with a flash column. For removing toluene and unreacted excessive cyclic polysiloxane, the filtrate was evaporated and the degassing under vacuum was carried out at 80° C. for 3 hours to give a colorless transparent viscous liquid. A viscosity was 514 poises (23° C.) according to an E-type viscometer. The hydrosilyl group in hydrogenated polyisoprene was confirmed as the strong peak of 2150 cm$^{-1}$ according to the IR spectra. By comparing the peak intensity of combined Si—CH$_3$ and SiCH$_2$— with that of the Si—H in 300 MHz NMR spectra, it was revealed that 1.2 hydrosilyl groups on the average per one molecule of said cyclic polysiloxane had been consumed. Namely, the polymer is hydrogenated polyisoprene having an increased molecular weight because of cyclic hydrogenpolysiloxane and having the following molecular end: 80° C. for 1 hour, the remaining allyl group in the reaction solution was determined by means of IR spectra analysis. The disappearance of carbon-carbon double bond peak at 1638 cm$^{-1}$ was confirmed.

Next, the content in the flask was transferred to a 300 ml ground-glass egg-plant flask and the degassing under vacuum was carried out at 80° C. for 3 hours so that toluene and excess cyclic polysiloxane was removed to give a colorless transparent viscous liquid.

A yield was calculated from an amount of the obtained polymer. $\overline{Mn}$ and $\overline{Mn}$ were determined by means of a GPC method. The terminal structure was determined by measuring and comparing the strength of the resonance signal of the proton assigned to each structure by means of $^1$H-NMR (300 MHz).

Yield: 96% (43 g)
$\overline{Mn}$=3,900, $\overline{Mw}/\overline{Mn}$=1.25
The number of Si groups per one molecule≅2.9
Namely, the polymer is SiH-terminated polyisobutylene having the following structure:

Example 6

A 200 ml four-necked flask equipped with a stirring rod, a dropping funnel, a thermometer, a three-way cock and a condenser was used. In the flask, 9.26 g (38.5 mmol) of a cyclic polysiloxane:

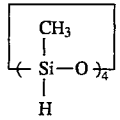

(LS 8600 manufactured by Shin-Etsu Chemical Co., Ltd.) and 20 ml of toluene were charged under a nitrogen atmosphere. A toluene solution in which 10 g of allyl group-containing acrylate ester polymer prepared in Preparative Example 5 and 16 μl of a solution of chloroplatinic acid catalyst (a solution in which H$_2$PtCl$_6$•6H$_2$O (1 g) is dissolved in ethanol (1 ml) and 1,2-dimethoxyethane (9 ml)) were dissolved in 30 ml of toluene was charged in the dropping funnel. The flask was heated to 70° C. and the toluene solution was dropwise added over 1 minute. After the addition was completed, the reaction was continued at 80° C. for 2 hours. At this time, the remaining allyl group in the reaction solution was determined by means of a IR spectra analysis. The disappearance of carbon-carbon double bond peak at 1645 cm$^{-1}$ was confirmed. Then, for removal of the catalyst remaining in the reaction system, 2 g of silica gel (Wakogel C-200 manufactured by Wako Junyaku Kabushiki Kaisha) was added and the reaction mixture was stirred at room temperature for 30 minutes and filtered with a flash column. For removing toluene and unreacted excessive cyclic polysiloxane, the filtrate was evaporated and the degassing under vacuum was carried out at 80° C. for 3 hours to give a colorless transparent viscous liquid. The hydrosilyl group in the acrylate ester polymer was confirmed as the strong peak of 2150 cm$^{-1}$ according to the IR spectra. By comparing the peak intensity of combined Si—CH$_3$ and SiCH$_2$ with that of the Si—H in 300 MHz NMR spectra, it was revealed that 1.10 hydrosilyl groups on the average per one molecule of said cyclic polysiloxane had been consumed. Namely, the polymer is a hydrosilyl group-containing acrylate ester polymer which has an increased molecular weight because of cyclic hydrogenpolysiloxane and has the following structure:

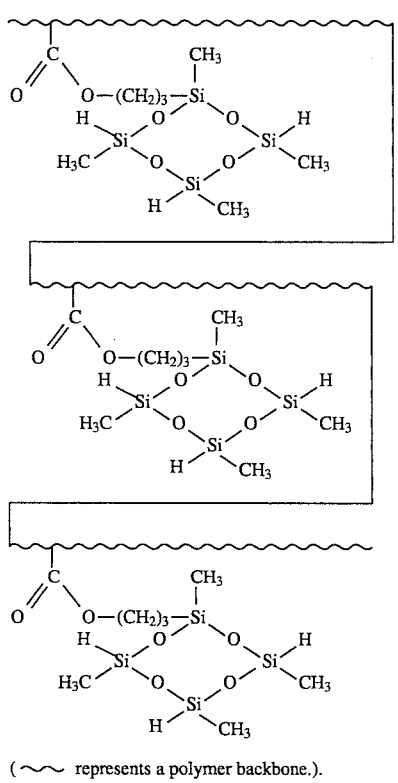

( ~~ represents a polymer backbone.).

Example 7

1.14 Grams of allyl ether-terminated polypropylene oxide prepared in Preparative Example 1, an amount indicated in Table 1 of hydrosilyl group-containing polypropylene oxide prepared in Example 1 and 10 μl of a chloroplatinic acid catalyst solution (a solution in which $H_2PtCl_6 \cdot 6H_2O$ (1 g) is dissolved in ethanol (10 ml) and 1,2-dimethoxyethane (90 ml)) were intimately mixed. A part of the mixture was transferred on a gelation testing device (manufactured by Nisshin Kagaku Kabushiki Kaisha) and the snap-up time (the time which is required for forming a rubbery elastomer) was measured at a given temperature. Results are shown in Table 1.

TABLE 1

| Amount of polymer of Example 1 | Molar ratio of hydrosilyl group to allyl | Measuring temperature | | |
|---|---|---|---|---|
| (g) | group* | 80° C. | 100° C. | 120° C. |
| 0.25 | 0.50 | 3' 27" | 1' 38" | 0' 53" |
| 0.38 | 0.75 | 2' 28" | 1' 07" | 0' 33" |
| 0.63 | 1.25 | 2' 06" | 0' 58" | 0' 31" |
| 0.75 | 1.50 | 2' 20" | 0' 56" | 0' 28" |
| 1.00 | 2.00 | 1' 55" | 0' 46" | 0' 27" |

*The molar ratio of hydrosilyl group to allyl group was determined from each strength ratio on the basis of methyl proton of a backbone in NMR spectra (the same hereinafter).

As clear from Table 1, the curing was effected rapidly, in particular at a high temperature of at least 100° C.

Example 8

The snap-up time was measured in the same manner as in Example 7 except that 1.75 g of hydrosilyl group-containing polypropylene oxide obtained in Example 2 was used instead of polypropylene oxide obtained in Example 1. Results are shown in Table 2. The curing was effected rapidly, in particular at a high temperature of at least 100° C.

TABLE 2

| Amount of polymer of Example 2 | Molar ratio of hydrosilyl group to allyl | Measuring temperature | | |
|---|---|---|---|---|
| (g) | group* | 80° C. | 100° C. | 120° C. |
| 0.25 | 0.50 | 5' 19" | 1' 13" | 0' 38" |
| 0.56 | 1.00 | 2' 54" | 0' 56" | 0' 25" |
| 0.75 | 1.50 | 2' 44" | 0' 44" | 0' 21" |
| 1.00 | 2.00 | 1' 56" | 0' 37" | 0' 17" |

Example 9

36.10 Grams of allyl ether-terminated polypropylene oxide prepared in Preparative Example 1, 13.10 g of hydrosilyl group-containing polypropylene oxide prepared in Example 1 (the molar ratio of the hydrosilyl group to the allyl group was 1 according to NMR spectra.) and 26 μl of a chloroplatinic acid catalyst solution used in Example 1 were intimately mixed with stirring. The mixture was defoamed by a centrifugal separation and cast in a mold made of polyethylene. The defoaming was again carried out at room temperature under a reduced pressure, and the mixture was cured at 100° C. for a given time to obtain a homogeneous rubbery cured material having a thickness of about 3 mm. A No. 3 dumbbell test piece according to JIS K 6301 was punched off from the sheet of the cured material, and a tensile test was carried out at a pulling speed of 200 mm/min. Results are shown in Table 3. The rubbery cured material exhibiting stable tensile properties was obtained in a short time of from 30 minutes to 1 hour.

TABLE 3

| Curing time (min) | $M_{10}$ kg/cm² | $M_{30}$ kg/cm² | $M_{50}$ kg/cm² | $M_{100}$ kg/cm² | $M_{150}$ kg/cm² | $T_B$ kg/cm² | $E_B$ % |
|---|---|---|---|---|---|---|---|
| 15 | 0.3 | 0.8 | 1.2 | 1.9 | 2.5 | 4.2 | 307 |
| 30 | 0.3 | 0.8 | 1.1 | 1.8 | 2.4 | 5.0 | 387 |
| 60 | 0.3 | 0.8 | 1.2 | 1.9 | 2.4 | 5.5 | 420 |

Example 10

A cured material was prepared and subjected to a tensile test in the same manner as in Example 9 by using 42.00 g of allyl ether-terminated polypropylene oxide prepared in Preparative Example 1, 12.00 g of hydrosilyl group-containing polypropylene oxide prepared in Example 2 (the molar ratio of the hydrosilyl group to the allyl group was 1 according to NMR spectra.) and 30 μl of a chloroplatinic acid catalyst solution used in Example 1. Results are shown in Table 4. The rubbery material exhibiting stable tensile properties was obtained in a very short time of from 5 to 15 minutes.

TABLE 4

| Curing time (min) | $M_{10}$ kg/cm² | $M_{30}$ kg/cm² | $M_{50}$ kg/cm² | $M_{100}$ kg/cm² | $M_{150}$ kg/cm² | $T_B$ kg/cm² | $E_B$ % |
|---|---|---|---|---|---|---|---|
| 5 | 0.3 | 0.7 | 1.1 | 1.6 | 2.1 | 4.0 | 378 |
| 10 | 0.4 | 0.9 | 1.3 | 2.0 | 2.5 | 4.0 | 302 |

TABLE 4-continued

| Curing time (min) | $M_{10}$ kg/cm² | $M_{30}$ kg/cm² | $M_{50}$ kg/cm² | $M_{100}$ kg/cm² | $M_{150}$ kg/cm² | $T_B$ kg/cm² | $E_B$ % |
|---|---|---|---|---|---|---|---|
| 15 | 0.3 | 0.9 | 1.3 | 2.0 | 2.6 | 3.8 | 272 |
| 30 | 0.3 | 0.9 | 1.3 | 2.0 | 2.6 | 4.2 | 301 |
| 60 | 0.4 | 0.9 | 1.4 | 2.1 | 2.6 | 4.6 | 329 |

Comparative Example 1

A cured material was prepared in the same manner as in Example 9 except that 1.54 g of a polymethylhydro-dimethylsiloxane copolymer (average molecular weight: about 2,000 to 2,100, PS 123 available from Chisso Kabushiki Kaisha) of the formula:

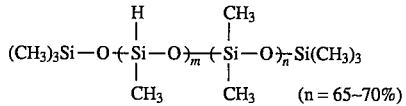

(the molar ratio of the hydrosilyl group to the allyl group was 1.) was used instead of the hydrosilyl group-containing polypropylene oxide prepared in Example 1. Said polysiloxane had poor compatibility with said allyl group-containing polypropylene oxide, and the mixture was opaque. Many foams remained after the defoaming under a reduced pressure. Only a cured material having bad mechanical properties and containing many foams was obtained.

Example 11

9.00 Grams of allyl ether-terminated polypropylene oxide prepared in Preparative Example 1, 3.18 g of hydrosilyl group-containing polypropylene oxide prepared in Example 1 (the molar ratio of the hydrosilyl group to the allyl group was 1.) and 6 μl of a chloroplatinic acid catalyst solution used in Example 1 were intimately mixed with stirring. The mixture was defoamed by a centrifugal separation and cast in a mold having a size of 6 cm (length) ×0.8 cm (width)×1.8 cm (depth). The defoaming was again carried out at a room temperature under a reduced pressure, and the mixture was cured at 100° C. for 30 minutes to obtain a rubbery cured material having a thickness of 13 mm. The hardness was measured according to a hardness measuring method defined in a spring-method hardness test (A type) in JIS K 6301, paragraph 5-2. The cured material had a hardness of 16 on the obverse and a hardness of 16 also on the reverse. The sample having good depth curability was obtained.

Example 12

The defoaming and the curing were carried out to give a rubbery cured material having a thickness of 13 mm in the same manner as in Example 11 by using 10.5 g of allyl ether-terminated polypropylene oxide prepared in Preparative Example 1, 3.00 g of hydrosilyl group-containing polypropylene oxide prepared in Example 2 (the molar ratio of the hydrosilyl group to the allyl group was 1.) and 7 μl of chloroplatinic acid catalyst solution used in Example 1. The obverse of the cured material had a hardness of 18 and the reverse had a hardness of 18.

Example 13

1.00 Grams of allyl ether-terminated polycaprolactone prepared in Preparative Example 2, 0.40 g of hydrosilyl group-containing polycaprolactone prepared in Example 3 and an amount indicated in Table 5 of chloroplatinic acid catalyst solution used in Example 3 were intimately mixed. A part of the mixture was transferred on a gelation testing device (manufactured by Nisshin Kagaku Kabushiki Kaisha) and the snap-up time (the time which is required for forming a rubbery elastomer) was measured at a given temperature. Results are shown in Table 5. The composition cured rapidly at a high temperature.

TABLE 5

| Amount of catalyst (μl) | Temperature | | |
|---|---|---|---|
| | 80° C. | 100° C. | 120° C. |
| 0.30 | 1' 24" | 0' 29" | 0' 18" |
| 1.49 | 1' 08" | 0' 20" | 0' 15" |
| 2.97 | 0' 53" | 0' 18" | 0' 14" |

Example 14

7.20 Grams of allyl ether-terminated polycaprolactone prepared in Preparative Example 2, 2.88 g of hydrosilyl group-containing polycaprolactone prepared in Example 3 (The molar ratio of the hydrosilyl group to the allyl group was 1 according to NMR spectra.) and 2.1 μl of chloroplatinic acid catalyst solution used in Example 3 were intimately mixed with stirring. The mixture was defoamed by a centrifugal separation and cast in a mold made of polyethylene. The defoaming was again carried out at a room temperature under a reduced pressure, and the mixture was cured at 100° C. for 30 minutes to obtain a homogeneous rubbery cured material having a thickness of about 3 mm. A No. 3 dumbbell according to JIS K 6301 was punched off from the sheet of cured material, and a tensile test was curried out at a tensile speed of 200 mm/min. $E_B$ was 400% and $T_B$ was 4.2 kg/cm². The cured material exhibiting a rubbery elasticity was obtained for a short time of 30 minutes.

Comparative Example 2

A cured material was prepared in the same manner as in Example 14 except that 0.965 g of a polymethylhydro-dimethylsiloxane copolymer (average molecular weight: about 2,000 to 2,100, PS 123 manufactured by Chisso Kabushiki Kaisha) of the formula:

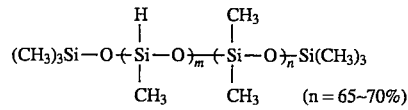

(the molar number of olefin of the polymer determined from a iodine value was the same as that of the hydrosilyl group of said polysiloxane.) was used in stead of hydrosilyl group-containing polycaprolactone prepared in Example 3. Said hydrogenpolysiloxane had poor compatibility with said allyl ether-terminated polycaprolactone, and the mixture was opaque. Many foams remained after the defoaming under a reduced pressure. Only a cured material containing many foams was obtained and a tensile test cannot be curried out.

Example 15

10.0 Grams of allyl ether-terminated polycaprolactone prepared in Preparative Example 2, 4.0 g of hydrosilyl group-containing polycaprolactone prepared in Example 3

(the molar ratio of the hydrosilyl group to the allyl group was 1.) and 3 μl of a chloroplatinic acid catalyst solution used in Example 3 were intimately mixed with stirring. The mixture was defoamed by a centrifugal separation and cast in a mold having a size of 6 cm (length) ×0.8 cm (width)×1.8 cm (depth). The defoaming was again carried out at a room temperature under a reduced pressure, and the mixture was cured at 100° C. for 30 minutes to obtain a rubbery cured material having a thickness of 13 mm. A hardness (Shore A hardness) was measured according to a hardness measuring method defined in a spring-method hardness test (A type) in JIS K 6301, paragraph 5-2. The cured material had a hardness of 20 on the obverse and a hardness of 18 on the reverse. This result reveals that the sample having good depth curability was obtained.

Example 16

1.00 Grams of allyl ether-terminated hydrogenated polyisoprene prepared in Preparative Example 3, an amount indicated in Table 6 of hydrosilyl group-containing hydrogenated polyisoprene prepared in Example 4 and 0.5 μl of a chloroplatinic acid catalyst solution used in Example 4 were intimately mixed. A part of the mixture was transferred on a gelation testing device (manufactured by Nisshin Kagaku Kabushiki Kaisha) and a snap-up time (the time which is required for forming a rubbery elastomer) was measured at a given temperature. Results are shown in Table 6.

TABLE 6

| Amount of polymer of Example 4 (g) | Molar ratio of hydrosilyl group to allyl group* | Measuring temperature | | |
|---|---|---|---|---|
| | | 80° C. | 100° C. | 120° C. |
| 0.087 | 0.25 | 14' 00" | 4' 46" | 1' 36" |
| 0.17 | 0.50 | 6' 26" | 1' 37" | 0' 34" |
| 0.33 | 1.0 | 3' 45" | 0' 53" | 0' 23" |
| 0.50 | 1.5 | 2' 49" | 0' 49" | 0' 23" |
| 0.66 | 2.0 | 3' 16" | 0' 51" | 0' 20" |
| 0.99 | 3.0 | 2' 36" | 1' 00" | 0' 28" |
| 1.65 | 5.0 | 5' 04" | 1' 47" | 0' 41" |

*The molar ratio of the hydrosilyl group to the allyl group is determined by comparing each strength on the basis of proton of the backbone in the NMR spectra.

The composition cured rapidly at a high temperature.

Example 17

45.0 grams of allyl ether-terminated hydrogenated polyisoprene prepared in Preparative Example 3, 15.0 g of hydrosilyl group-containing polyisoprene prepared in Example 4 (the molar ratio of the hydrosilyl group to allyl group was 1 according to NMR spectra.) and 25 μl of chloroplatinic acid catalyst solution used in Example 4 were intimately mixed with stirring. The mixture was defoamed by a centrifugal separation and cast in a mold made of polyethylene. The defoaming was again carried out at a room temperature under a reduced pressure, and the mixture was cured at 100° C. for a given time to obtain a homogeneous rubbery cured material having a thickness of about 3 mm. A No. 3 dumbbell test piece according to JIS K 6301 was punched off from the sheet of the cured material, and a tensile test was carried out at a tensile speed of 200 mm/min. Results are shown in Table 7. The rubbery cured material exhibiting stable tensile properties was obtained in a short time of from 30 minutes to 1 hour.

TABLE 7

| Curing time (min) | $M_{10}$ kg/cm² | $M_{30}$ kg/cm² | $M_{50}$ kg/cm² | $T_B$ kg/cm² | $E_B$ % |
|---|---|---|---|---|---|
| 10 | 0.8 | 1.7 | 2.6 | 3.4 | 80 |
| 15 | 0.6 | 1.5 | 2.1 | 2.9 | 83 |
| 30 | 1.2 | 2.7 | 3.9 | 5.2 | 66 |
| 45 | 1.4 | 3.0 | 4.5 | 5.5 | 60 |
| 60 | 1.2 | 2.9 | 4.3 | 6.0 | 80 |
| 90 | 1.0 | 2.8 | 4.0 | 5.2 | 70 |
| 120 | 1.2 | 3.0 | 4.1 | 5.5 | 75 |

Comparative Example 3

A cured material was prepared in the same manner as in Example 17 except that 3.64 g of a polymethylhydrodimethylsiloxane copolymer (average molecular weight: about 2,000 to 2,010, PS 123 manufactured by Chisso Kabushiki Kaisha) of the formula:

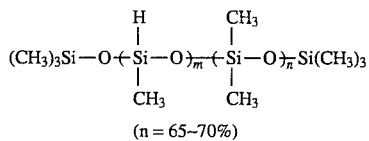

(n = 65~70%)

(the molar number of the olefin of the polymer of Preparative Example 3 determined from a iodine value was the same as that of the hydrosilyl group of said polysiloxane.) was used in stead of hydrosilyl group-containing polyisoprene prepared in Example 4. Said hydrogensiloxane had poor compatibility with said allyl ether-terminated hydrogenated polyisoprene, and the mixture was opaque. Much foaming occurred after the defoaming under a reduced pressure. Only a cured material having bad mechanical properties and containing many foams was obtained. A tensile test cannot be carried out.

Example 18

9.10 Grams of allyl ether-terminated hydrogenated polyisoprene prepared in Preparative Example 3, 3.03 g of hydrosilyl group-containing hydrogenated polyisoprene prepared in Example 4 (the molar ratio of the hydrosilyl group to the allyl group was 1.) and 5 μl of a chloroplatinic acid catalyst solution used in Example 4 were intimately mixed with stirring. The mixture was defoamed by a centrifugal separation and cast in a mold having a size of 6 cm (length)×0.8 cm (width)×1.8 cm (depth). The defoaming was again carried out at a room temperature under a reduced pressure, and the mixture was cured at 100° C. for 30 minutes to obtain a rubbery cured material having a thickness of 13 mm. The hardness (Shore A hardness) was measured according to a hardness measuring method defined in a spring-method hardness test (A type) in JIS K 6301, paragraph 5-2. The cured material had a hardness of 36 on the obverse and a hardness of 38 on the reverse. The sample having good depth curability was obtained.

Example 19

3 Grams of allyl-terminated polyisobutylene prepared in Preparative Example 4, 1 g of SiH-terminated polyisobutylene prepared in Example 5 and 0.5 μl of a chloroplatinic acid catalyst solution used in Example 5 were intimately mixed with stirring. A part of the mixture was transferred on a gelation testing device and a snap-up time was measured in the same manner as in Example 7. The snap-up time was 50 seconds at 100° C. After the mixture was cast in a mold having a thickness of 3 mm, it was heated in an oven at 100° C. for 5 minutes to obtain a homogeneous rubbery cured material. A No. 3 dumbbell test piece according to JIS K 6301 was punched off from the sheet of the cured material, and a tensile test was curried out at a pulling speed of 200 mm/min. $M_{50}$ was 3.8 kg/cm$^2$, $T_B$ was 5.1 kg/cm$^2$ and $E_B$ was 70%. The rubbery cured material having a tack-free surface and exhibiting stable tensile properties was obtained for a short time of a few minutes.

Example 20

The same composition used in Example 19 was cast in a polyethylene sample tube having a diameter of about 1.5 cm and a length of about 10 cm. The composition was defoamed by a centrifugal separation and then cured at 100° C. for 10 minutes. After the curing, the polyethylene sample tube was cut at a bottom portion and cut surfaces were observed. The homogeneous curing was effected.

Example 21

30 Grams of allyl group-containing acrylate ester polymer prepared in Preparative Example 5, 10 g of hydrosilyl group-containing acrylate ester polymer prepared in Example 6 and 50 μl of a chloroplatinic acid catalyst solution used in Example 6 were intimately mixed with stirring. The mixture was defoamed by a centrifugal separation and cast in a mold made of polyethylene. The defoaming was again carried out at room temperature under a reduced pressure, and then the mixture was cured at 100° C. for 30 minutes to obtain a homogeneous transparent rubbery elastic material.

Example 22

The same composition used in Example 21 was cast in a mold having a thickness of about 18 mm. In the same manner, the composition was defoamed at room temperature under a reduced pressure and then cured at 100° C. for 30 minutes. A homogeneous rubbery elastic material having a thickness of about 13 mm was obtained. The hardness of the obverse was 32 (Shore A hardness) and the hardness of the reverse was 31 (Shore A hardness). An internal part also cured homogeneously.

Comparative Example 4

A cured material was prepared in the same manner as in Example 21 except that 10.8 g of a polymethylhydrodimethylsiloxane copolymer (average molecular weight: about 2,000 to 2,100, PS 123 manufactured by Chisso Kabushiki Kaisha) of the formula:

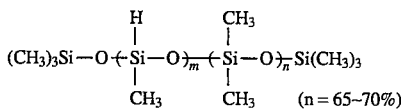

(n = 65–70%)

was used in stead of hydrosilyl group-containing acrylate ester polymer prepared in Example 6. Said hydrogenpolysiloxane had poor compatibility with said allyl group-containing acrylate ester polymer, and the mixture was opaque. Many foams remained after the defoaming under a reduced pressure. Only a cured material containing many foams was obtained, and a tensile test cannot be carried out.

BRIEF DESCRIPTION OF THE DRAWINGS

FIG. 1 is a chart of allyl ether-terminated polypropylene oxide in Preparative Example 1, FIG. 2 is a magnified chart of an allyl group portion —OCH$_2$—C$\underline{H}$=CH$_2$ in allyl ether-terminated polypropylene oxide in Preparative Example 1 (the magnification power is 749 times.), FIG. 3 is a magnified chart of an allyl group portion —OCH$_2$—CH=C$\underline{H}_2$ in allyl ether-terminated polypropylene oxide in Preparative Example 1 (the magnification power is 435 times.), FIG. 4 is a chart of hydrosilyl group-containing polypropylene oxide in Example 1, FIG. 5 is a magnified chart of the Si—C$\underline{H}_3$ and Si—C$\underline{H}_2$—CH$_2$—CH$_2$—O— portions in hydrosilyl group-containing polypropylene oxide in Example 1 (the magnification power is 40 times.), FIG. 6 is a magnified chart of the Si—$\underline{H}$ portion in hydrosilyl group-containing polypropylene oxide in Example 1 (the magnification power is 97 times.), and FIG. 7 is a magnified chart of hydrosilyl group-containing polypropylene oxide in Example 1 at about 5.0 to 6.2 ppm. It is revealed that the allyl group completely disappeared and hydrosilylation occurred.

Figure 1:
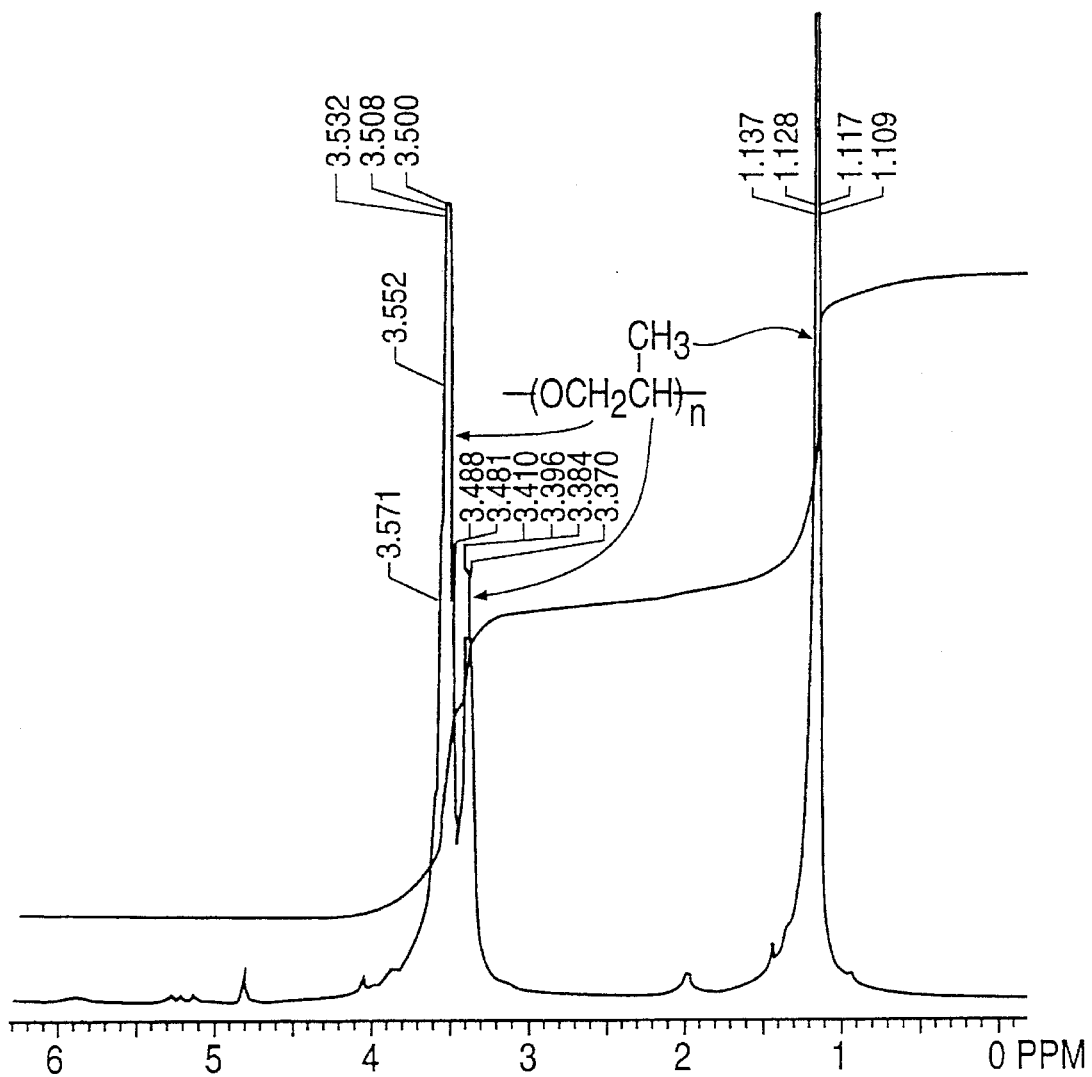
FIGS. 1 to 7 each shows a 300 MHz NMR spectra chart.
Figure 2:
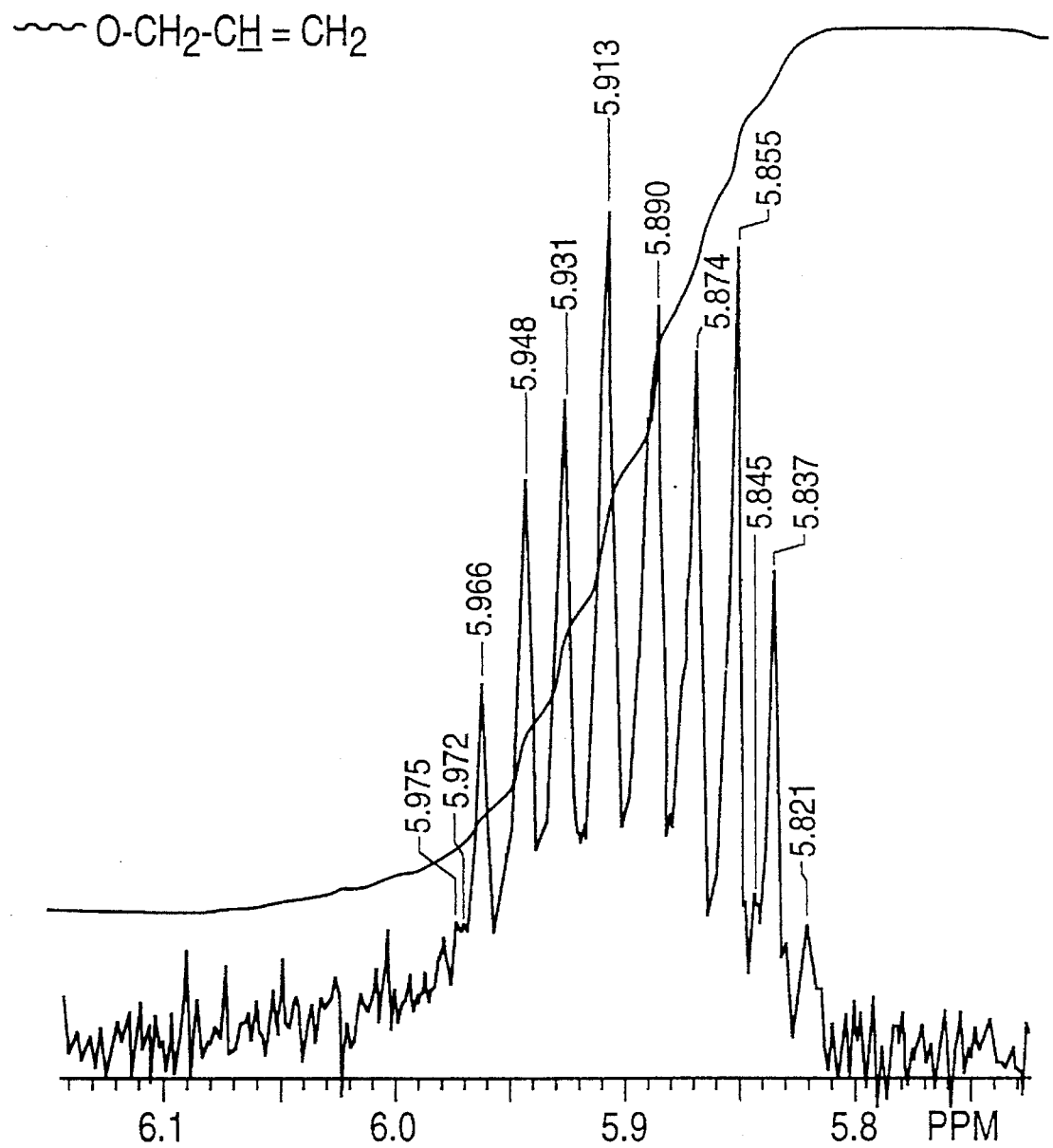
Figure 3:
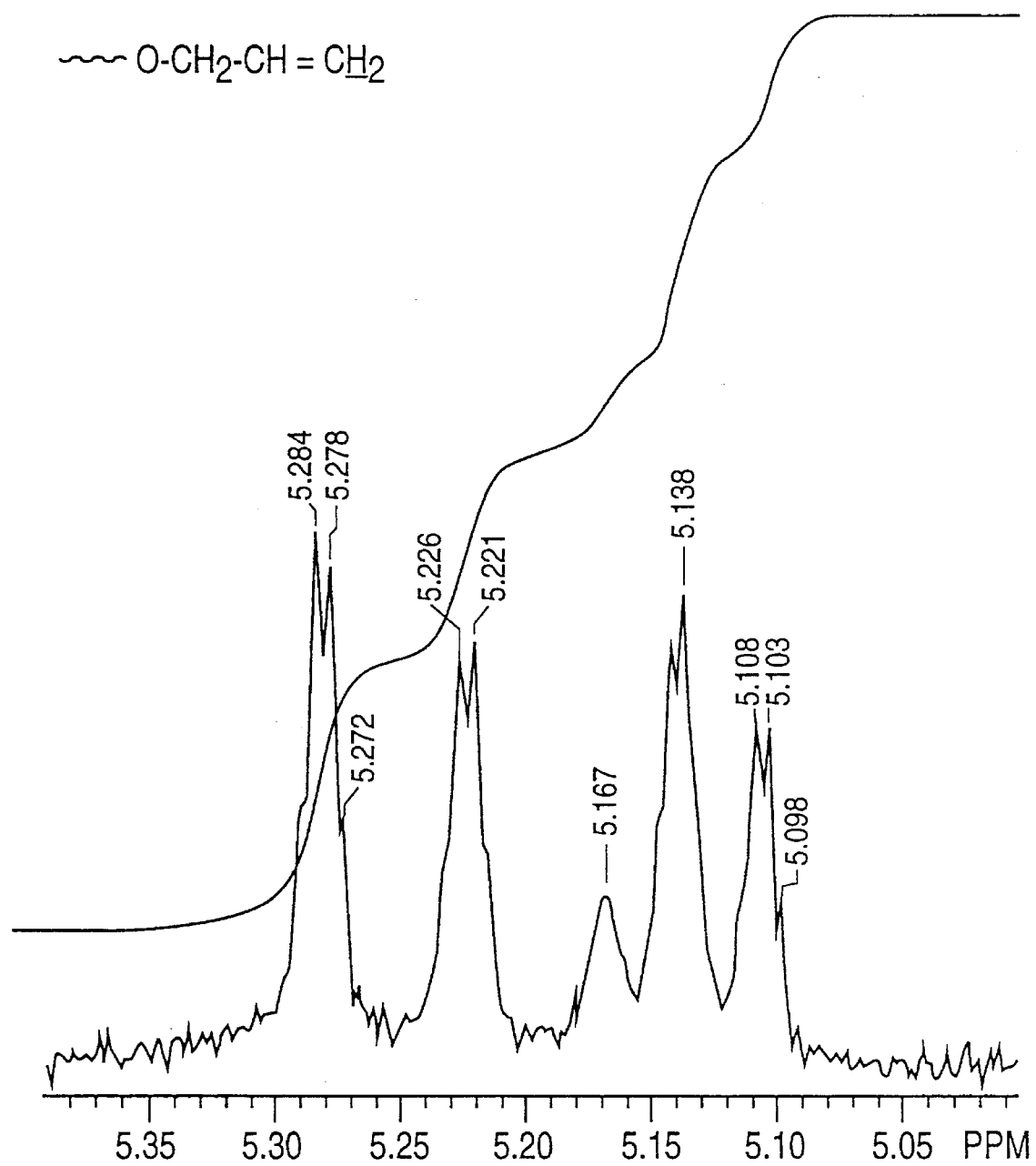

(1) As is clear from FIGS. 1 and 2, 126 backbone protons

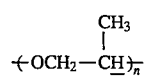

correspond to one proton (—OCH$_2$—C$\underline{H}$=CH$_2$) of the allyl group.

Figure 4:
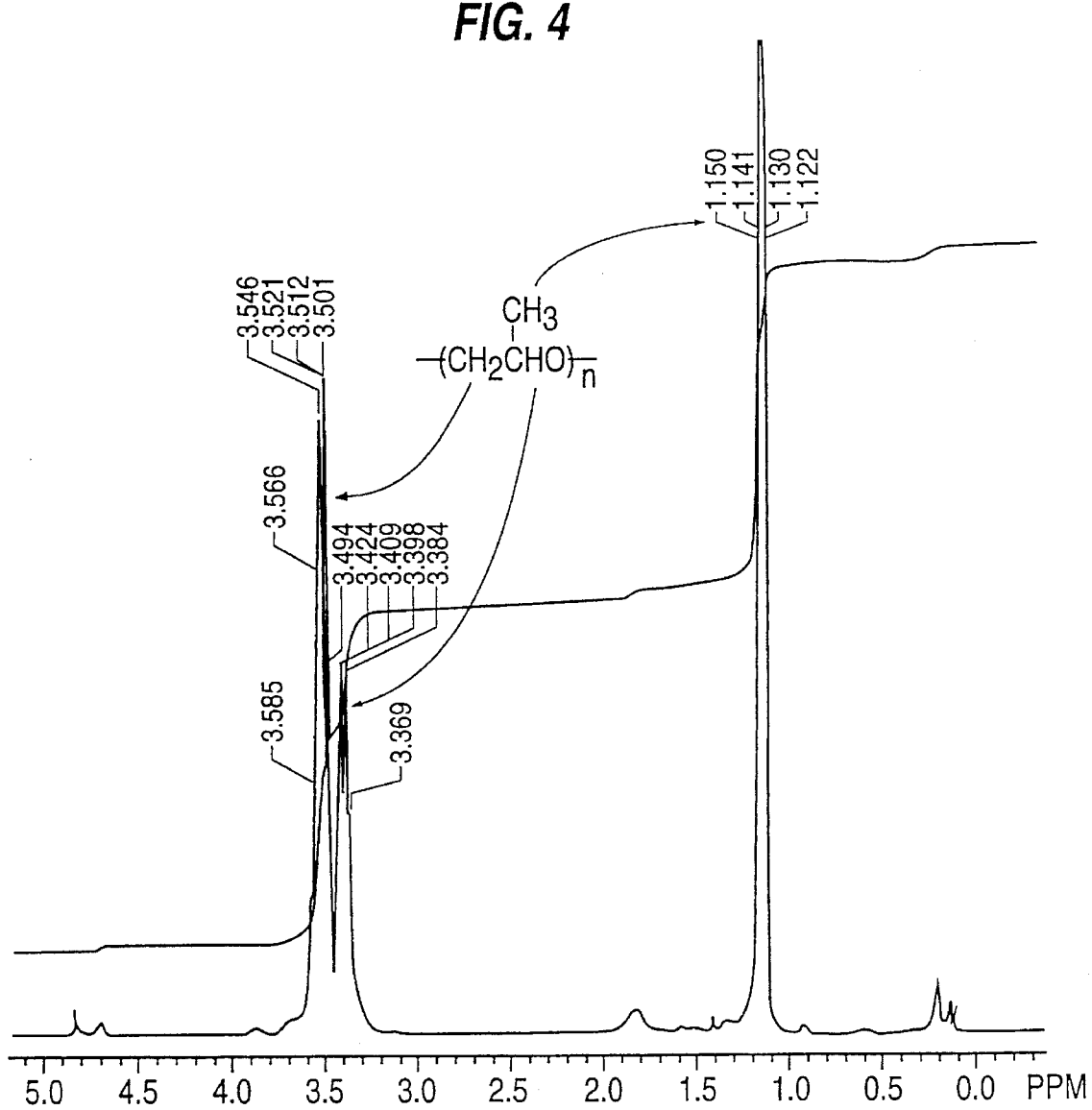
Figure 5:
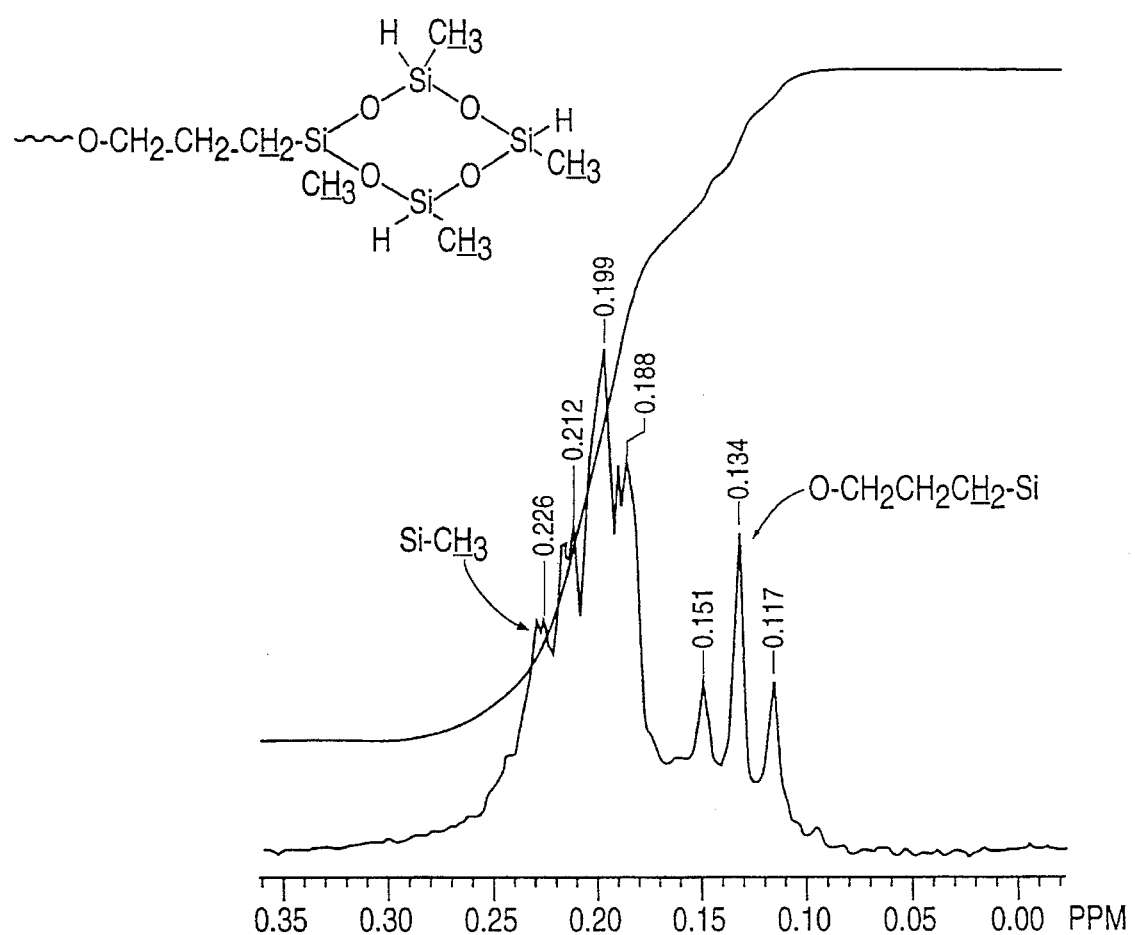

(2) As is clear from FIGS. 4 and 5, 116 backbone protons

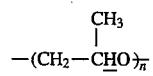

correspond to one proton of the —Si—C$\underline{H}_3$ and —Si—C$\underline{H}_2$.

Figure 6:
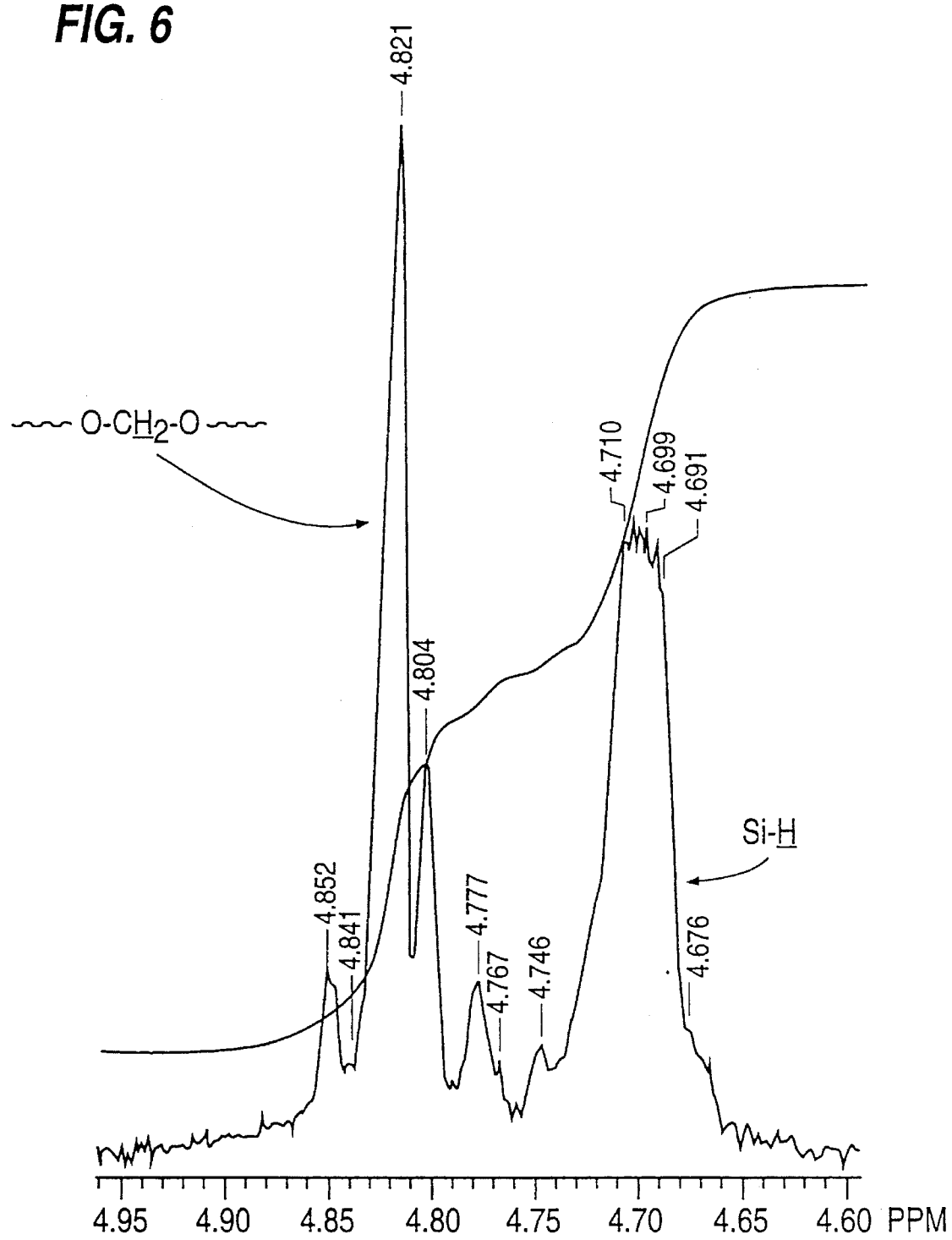
Figure 7:
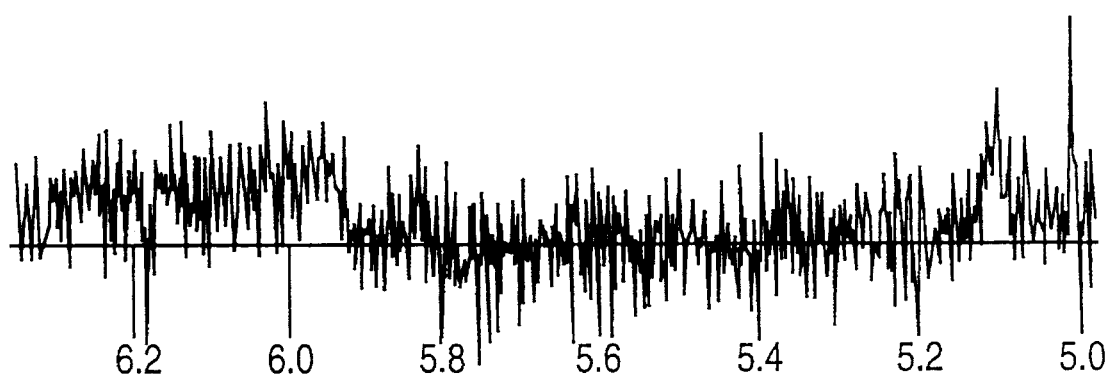

(3) As is clear from FIGS. 4 and 6, 45 backbone protons

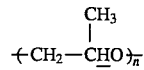

correspond to one proton of the —Si—$\underline{H}$.

(4) From the results of (1) and (3), a molar ratio of the allyl group to the hydrosilyl group is 1.0/2.8.

(5) From FIGS. 5 and 6, Si—$\underline{H}$/Si—C$\underline{H}_2$+Si—C$\underline{H}_3$ is 0.184.

The polymer generally comprises the following polymers (IV) and (V):

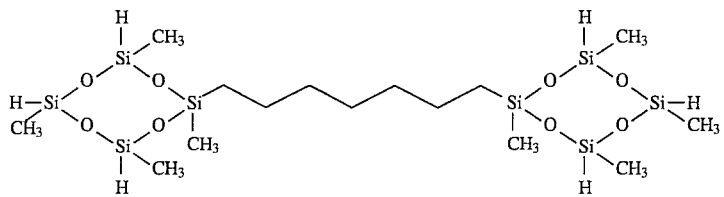

(IV)

and

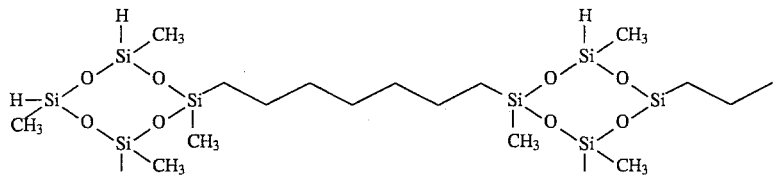

(V)

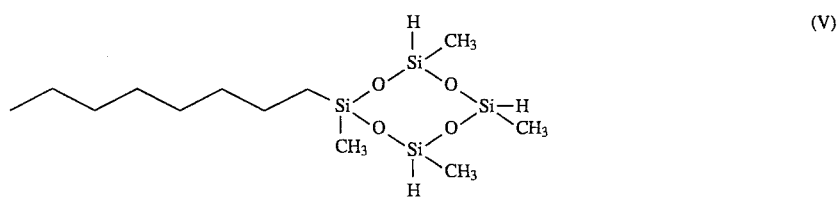

In the case of (IV)

Si—H/(Si—CH$_2$—+Si—CH$_3$)=6/28=0.214

In the case of (V)

Si—H/(Si—CH$_2$— + Si—CH$_3$) = 8/44 = 0.182

$$1 + 0.33 \times \frac{0.214 - 0.184}{0.214 - 0.182} = 1 + 0.33 \times \frac{0.030}{0.032} = 1.31$$

Therefore, in Example 1, 1.31 Si—H groups on the average in one molecule of cyclic hydrogenpolysiloxane are used for the hydrosilylation reaction and residual 2.69 groups are present as Si—H group in the molecule.

We claim:

1. A curable composition which comprises (C) a first organic polymer having at least two hydrosilyl groups of formula

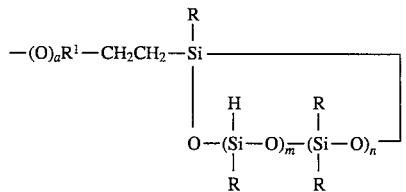

wherein each R is H, OSi(CH$_3$)$_3$ or an organic group having 1 to 10 carbon atoms, R$^1$ is selected from the divalent group consisting of

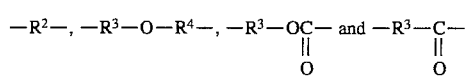

wherein R$^2$, R$^3$ and R$^4$ are divalent hydrocarbon groups having 1 to 20 carbon atoms, a is 0 or 1 and wherein (i) $m \geq 1$; and (ii) $m+n=2\sim 50$, the backbone of said first organic polymer is selected from the group consisting of (meth)acrylate ester polymers, hydrocarbon polymers and polyester polymers, (D) a second organic polymer having at least one alkenyl group, said second organic polymer selected from the group consisting of (meth)acrylate ester polymers, hydrocarbon polymers and polyester polymers wherein the backbone of said first and second polymers are both either (meth)acrylate ester polymers, hydrocarbon polymers, or polyester polymers, and (E) a hydrosilylation catalyst.

2. The composition according to claim 1, wherein the component (C) has a molecular weight of from 500 to 50,000, the component (D) has a molecular weight of from 500 to 50,000, and a molar ratio of the hydrosilyl group of the component (C) to the alkenyl group of the component (D) is from 0.2 to 5.0.

3. The composition according to claim 1, wherein the component (C) is a hydrosilyl group-containing organic polymer which has a molecular weight of from 500 to 50,000 and has, in a molecular chain or at a molecular end, at least one hydrosilyl group of the formula:

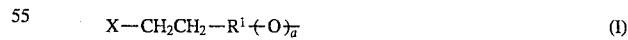

wherein X is a group selected from the group consisting of:

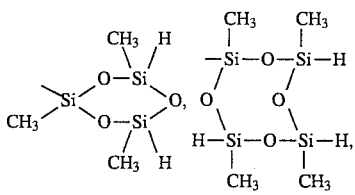

-continued $$\begin{array}{c}
\text{CH}_3 \quad \text{CH}_3 \\
| \quad \quad | \\
-\text{Si}-\text{O}-\text{Si}-\text{O} \\
/ \quad \quad \quad \text{H} \quad | \quad \text{CH}_3 \\
\text{O} \quad \quad \quad \quad \text{Si} \\
\backslash \quad \quad \quad \text{H} \quad | \quad \backslash \text{H} \\
\text{H}-\text{Si}-\text{O}-\text{Si}-\text{O} \\
| \quad \quad | \\
\text{CH}_3 \quad \text{CH}_3
\end{array},$$

$$-\overset{\text{CH}_3}{\underset{|}{\text{Si}}}-\left[\text{O}\left(\underset{\text{H}}{\overset{\text{CH}_3}{\text{Si}}}-\text{O}\right)_{\!\!2}\!\!\left(\underset{\text{CH}_3}{\overset{\text{CH}_3}{\text{Si}}}-\text{O}\right)\right]-,$$

$$-\overset{\text{CH}_3}{\underset{|}{\text{Si}}}-\left[\text{O}\left(\underset{\text{H}}{\overset{\text{CH}_3}{\text{Si}}}-\text{O}\right)\!\!\left(\underset{\text{CH}_3}{\overset{\text{CH}_3}{\text{Si}}}-\text{O}\right)_{\!\!2}\right]-,$$

$$\text{CH}_3\underset{|}{\overset{|}{\text{Si}}}\begin{array}{l}
(\text{O}-\overset{\text{CH}_3}{\underset{\text{H}}{\text{Si}}})_p\text{OSi}(\text{CH}_3)_3 \\
\\
(\text{O}-\overset{\text{H}}{\underset{\text{CH}_3}{\text{Si}}})_q\text{OSi}(\text{CH}_3)_3
\end{array}$$

(wherein p and q is 0 or a positive integer provided that $2 \leq p+q \leq 4$.), $R^1$ is a group selected from divalent groups of the formulas:

$$-R^2-,\ -R^3-O-R^4-,\ -R^3-\underset{\underset{O}{\|}}{OC}-\ \text{and}\ -R^3-\underset{\underset{O}{\|}}{C}-$$

(wherein $R^2$, $R^3$ and $R^4$ are divalent hydrocarbon groups having 1 to 20 carbon atoms.), and a is 0 or 1.

4. The composition according to claim 1, wherein the hydrosilyl group-containing organic polymer (C) is a polyether polymer.

5. The composition according to claim 1, wherein the hydrosilyl group-containing organic polymer (C) is a polyester polymer.

6. The composition according to claim 30, wherein the hydrosilyl group-containing organic polymer (C) is a polymer which comprises an aliphatic polyester.

7. The composition according to claim 1, wherein the hydrosilyl group-containing organic polymer (C) is a hydrocarbon polymer.

8. The composition according to claim 7, wherein the component (C) is selected from the group consisting of polyisobutylene, hydrogenated polyisoprene, hydrogenated polybutadiene and copolymers thereof.

9. The composition according to claim 1, wherein the hydrosilyl group-containing organic polymer (C) is a (meth)acrylate ester polymer.

10. The composition according to claim 9, wherein the component (C) is a polymer which is prepared by polymerizing at least one monomer selected from the group consisting of ethyl acrylate, butyl acrylate, allyl acrylate, methyl methacrylate, butyl methacrylate and allyl methacrylate, or prepared by polymerizing at least one monomer selected from the above acrylates and methacrylates and at least one copolymerizable monomer selected from the group consisting of styrene, vinyl acetate and acrylonitrile.

11. The composition according to claim 1, wherein the hydrosilyl group-containing organic polymer (C) is a polycarbonate polymer.

12. The composition according to claim 1, wherein the hydrosilyl group of the organic polymer (C) is present at a molecular end.

13. The composition according to claim 1, the organic polymer (D) has a molecular weight of from 500 to 50,000 and has at least one alkenyl group of the formula:

$$\text{CH}_2=\overset{R^5}{\underset{|}{\text{C}}}-R^1\!+\!\text{O}\!\!\rightarrow_{\!\!a} \quad (\text{III})$$

wherein $R^1$ is a group selected from divalent groups of the formulas:

$$-R^2-,\ -R^3-O-R^4-,\ -R^3-\underset{\underset{O}{\|}}{OC}-\ \text{and}\ -R^3-\underset{\underset{O}{\|}}{C}-$$

wherein $R^2$, $R^3$ and $R^4$ are divalent hydrocarbon groups having 1 to 20 carbon atoms, $R^5$ is hydrogen or a methyl group, and a is 0 or 1.

14. The composition according to claim 1, wherein the alkenyl group-containing organic polymer (D) has good compatibility with the component (C).

15. The composition according to claim 1, wherein the components (C) and (D) both are a polyether polymer.

16. The composition according to claim 15, wherein the components (C) and (D) both are at least one selected from the group consisting of polyoxyethylene, polyoxypropylene, polyoxytetramethylene and copolymers thereof.

17. The composition according to claim 1, wherein the components (C) and (D) both are a polyester polymer.

18. The composition according to claim 1, wherein the components (C) and (D) both are a hydrocarbon polymer.

19. The composition according to claim 18, wherein the components (C) and (D) both are selected from the group consisting of polyisobutylene, hydrogenated polyisoprene, hydrogenated polybutadiene, 1,4-polybutadiene, 1,2-polybutadiene and copolymers thereof.

20. The composition according to claim 1, wherein the components (C) and (D) both are a (meth)acrylate ester polymer.

21. The composition according to claim 1, wherein the components (C) and (D) both are a polycarbonate polymer.

22. The composition according to claim 1, wherein the alkenyl group-containing organic polymer (D) is a polyether polymer.

23. The composition according to claim 1, wherein the alkenyl group-containing organic polymer (D) is a polyester polymer.

24. The composition according to claim 1, wherein the alkenyl group-containing organic polymer (D) is a hydrocarbon polymer.

25. The composition according to claim 1, wherein the alkenyl group-containing organic polymer (D) is a (meth)acrylate ester polymer.

26. The composition according to claim 1, wherein the alkenyl group-containing organic polymer (D) is a polycarbonate polymer.

* * * * *